United States Patent
Yamashita et al.

(10) Patent No.: US 10,273,191 B2
(45) Date of Patent: Apr. 30, 2019

(54) TRANSLUCENT ZIRCONIA SINTERED BODY, METHOD FOR MANUFACTURING SAME, AND USE THEREOF

(71) Applicant: TOSOH CORPORATION, Yamaguchi (JP)

(72) Inventors: Isao Yamashita, Kanagawa (JP); Yuya Machida, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 15/540,683

(22) PCT Filed: Jan. 12, 2016

(86) PCT No.: PCT/JP2016/050717
§ 371 (c)(1),
(2) Date: Jun. 29, 2017

(87) PCT Pub. No.: WO2016/114265
PCT Pub. Date: Jul. 21, 2016

(65) Prior Publication Data
US 2017/0349494 A1  Dec. 7, 2017

(30) Foreign Application Priority Data

Jan. 15, 2015  (JP) .................................. 2015-005981
Nov. 30, 2015  (JP) .................................. 2015-233643

(51) Int. Cl.
| | | |
|---|---|---|
| C04B 35/48 | (2006.01) | |
| A61C 13/083 | (2006.01) | |
| C04B 35/645 | (2006.01) | |
| A61C 7/14 | (2006.01) | |
| A61C 5/70 | (2017.01) | |
| C04B 35/486 | (2006.01) | |

(52) U.S. Cl.
CPC ............ *C04B 35/6455* (2013.01); *A61C 5/70* (2017.02); *A61C 7/14* (2013.01); *A61C 13/083* (2013.01); *C04B 35/486* (2013.01); *C04B 2235/3206* (2013.01); *C04B 2235/3208* (2013.01); *C04B 2235/3225* (2013.01); *C04B 2235/3227* (2013.01); *C04B 2235/3229* (2013.01); *C04B 2235/5409* (2013.01); *C04B 2235/602* (2013.01); *C04B 2235/6565* (2013.01); *C04B 2235/661* (2013.01); *C04B 2235/762* (2013.01); *C04B 2235/765* (2013.01); *C04B 2235/78* (2013.01); *C04B 2235/786* (2013.01); *C04B 2235/80* (2013.01)

(58) Field of Classification Search
CPC ...... C04B 35/48; C04B 35/486; C04B 35/488; A61C 13/083
See application file for complete search history.

(56) References Cited

U.S. PATENT DOCUMENTS

| | | | |
|---|---|---|---|
| 4,067,745 A | | 1/1978 | Garvie et al. |
| 4,758,541 A | | 7/1988 | Tsukuma |
| 5,017,532 A | * | 5/1991 | Sonnenberg .......... C04B 35/486 501/103 |
| 8,598,058 B2 | * | 12/2013 | Mathers ................ B82Y 30/00 106/35 |
| 8,969,227 B2 | * | 3/2015 | Mathers ................ B82Y 30/00 106/35 |
| 9,592,105 B2 | * | 3/2017 | Hauptmann ....... A61C 13/0022 |
| 9,925,126 B2 | * | 3/2018 | Kolb ..................... C01G 25/00 |
| 2010/0003630 A1 | | 1/2010 | Yamashita et al. |
| 2011/0027742 A1 | | 3/2011 | Fujisaki et al. |
| 2012/0264588 A1 | * | 10/2012 | Kolb ..................... B82Y 30/00 501/134 |
| 2012/0277088 A1 | * | 11/2012 | Mathers ................ B82Y 30/00 501/134 |
| 2015/0157430 A1 | * | 6/2015 | Hauptmann .......... C04B 41/501 428/312.8 |
| 2015/0238291 A1 | * | 8/2015 | Hauptmann ....... A61C 13/0022 428/64.1 |

(Continued)

FOREIGN PATENT DOCUMENTS

| | | |
|---|---|---|
| GB | 2 206 11 | 12/1988 |
| JP | 62-91467 | 4/1987 |

(Continued)

OTHER PUBLICATIONS

International Search Report issued in Patent Application No. PCT/JP2016/050717, dated Mar. 15, 2016.

(Continued)

*Primary Examiner* — Karl E Group
(74) *Attorney, Agent, or Firm* — Greenblum & Bernstein, P.L.C.

(57) ABSTRACT

Provided is a zirconia sintered body having both high translucency and high strength. The zirconia sintered body includes crystal grains that include a cubic domain and a tetragonal domain, wherein a stabilizer and lanthanum is dissolved as a solid solution therein. The sintered body can be obtained by a manufacturing method including: a mixing step of obtaining a mixed powder by mixing a zirconia source, a stabilizer source, and a lanthanum source; a molding step of obtaining a green body by molding the obtained mixed powder; a sintering step of obtaining a sintered body by sintering the obtained green body at a sintering temperature of 1650° C. or higher; and a temperature lowering step of lowering the temperature from the sintering temperature to 1000° C. at a temperature lowering rate exceeding 1° C./min.

10 Claims, 10 Drawing Sheets

(56) References Cited

U.S. PATENT DOCUMENTS

2015/0282905 A1* 10/2015 Jahns .................. A61K 6/0245
433/167

FOREIGN PATENT DOCUMENTS

| | | |
|---|---|---|
| JP | 62-235255 | 10/1987 |
| JP | 2000-95564 | 4/2000 |
| JP | 2008-050247 | 3/2008 |
| JP | 2008-222450 | 9/2008 |
| JP | 2009-269812 | 11/2009 |
| JP | 2010-285328 | 12/2010 |
| JP | 2013-515671 | 5/2013 |

OTHER PUBLICATIONS

Matsui et al., "Cubic-Formation and Grain-Growth Mechanisms in Tetragonal Zirconia Polycrystal", Journal of the American ceramic society, vol. 86, No. 8, pp. 1401-1408, 2003.

* cited by examiner

TRANSLUCENT ZIRCONIA SINTERED BODY, METHOD FOR MANUFACTURING SAME, AND USE THEREOF

TECHNICAL FIELD

The present invention relates to a zirconia sintered body having high translucency and strength, and the method for manufacturing the zirconia sintered body.

BACKGROUND ART

A sintered body that contains zirconia as a main component and that has translucency (hereinafter, also referred to as "translucent zirconia sintered body") has superior mechanical properties compared to those of glass and alumina. Because of this, translucent zirconia sintered bodies have been investigated as materials for application purposes requiring mechanical properties as well as optical properties.

For example, Patent Document 1 discloses a translucent zirconia sintered body as a material suitable for a dental material, an exterior member, and the like. This translucent zirconia sintered body is a zirconia sintered body containing 3 mol % of yttria.

Patent Document 2 discloses a translucent zirconia sintered body as a material suitable for a dental material, especially an orthodontic bracket. This translucent zirconia sintered body is a zirconia sintered body containing 8 mol % of yttria.

Patent Document 3 discloses a zirconia sintered body as a material suitable for a dental material, especially an artificial tooth and a mill blank for obtaining an artificial tooth. This zirconia sintered body is a zirconia sintered body containing yttria and titania.

CITATION LIST

Patent Literature

Patent Document 1: Japanese Unexamined Patent Application Publication No. 2008-050247A
Patent Document 2: Japanese Unexamined Patent Application Publication No. 2009-269812A
Patent Document 3: Japanese Unexamined Patent Application Publication No. 2008-222450A

SUMMARY OF INVENTION

Technical Problem

With a conventional zirconia sintered body, strength is decreased as translucency is increased when the content of the stabilizer in the zirconia is increased. On the other hand, with a conventional zirconia sintered body, strength is increased as translucency is decreased when the content of the stabilizer is decreased. As described above, conventionally, zirconia sintered bodies either had high translucency or high strength.

An object of the present invention is to solve these problems and to provide a zirconia sintered body having both high translucency and strength.

Solution to Problem

The present researchers investigated a zirconia sintered body having translucency. As a result, it was found that a sintered body having both strength and translucency was obtained by controlling a structure within a crystal grain. Furthermore, it was also found that such a structure within a crystal grain was controlled by dissolving lanthanum in zirconia as a solid solution.

That is, the main points of the present invention are the following [1] to [10].

[1] A zirconia sintered body containing a crystal grain having a cubic domain and a tetragonal domain, a stabilizer and lanthanum being dissolved as a solid solution in the zirconia sintered body.

[2] The zirconia sintered body according to [1] above, where an average crystallite size calculated from the full-width at half maximum of $2\theta=30\pm2°$ in a powder X-ray diffraction pattern using CuKα as a radiation source is 255 nm or less.

[3] The zirconia sintered body according to [1] or [2] above, where an average crystallite size calculated from the full-width at half maximum of $2\theta=30\pm2°$ in a powder X-ray diffraction pattern using CuKα as a radiation source is 100 nm or less.

[4] The zirconia sintered body according to any one of [1] to [3] above, where a lanthanum content is 1 mol % or greater but 10 mol % or less.

[5] The zirconia sintered body according to any one of [1] to [4] above, where the stabilizer is at least one type selected from the group consisting of yttria, scandia, calcia, magnesia, and ceria.

[6] The zirconia sintered body according to any one of [1] to [5] above, where a bending strength is 500 MPa or greater.

[7] The zirconia sintered body according to any one of [1] to [6] above, where a total light transmittance using illuminant D65 as a radiation source is 45% or greater when a sample thickness is 1 mm.

[8] A method of manufacturing the zirconia sintered body described in any one of [1] to [7] above, the method including: a mixing step of obtaining a mixed powder by mixing a zirconia source, a stabilizer source, and a lanthanum source; a molding step of obtaining a green body by molding the obtained mixed powder; a sintering step of obtaining a sintered body by sintering the obtained green body at a sintering temperature of 1650° C. or higher; and a temperature lowering step of lowering the temperature from the sintering temperature to 1000° C. at a temperature lowering rate exceeding 1° C./min.

[9] The manufacturing method according to [8] above, where the sintering step includes a primary sintering of obtaining a primary sintered body by sintering at 1000° C. or higher but lower than 1650° C., and a secondary sintering of sintering the primary sintered body at 1650° C. or higher.

[10] A dental component containing the zirconia sintered body described in any one of [1] to [7] above.

The zirconia sintered body of the present invention will be described below.

The zirconia sintered body of the present invention is a lanthanum (La)-dissolved zirconia sintered body in which lanthanum is not simply contained in the sintered body but the lanthanum is dissolved in the zirconia as a solid solution. By allowing lanthanum to be dissolved to be a solid solution, the structure in the crystal grains of the sintered body becomes fine.

In the zirconia sintered body of the present invention (hereinafter, also referred to as "sintered body of the present invention"), it can be confirmed from a powder X-ray diffraction (hereinafter, also referred to as "XRD") pattern that the lanthanum is dissolved in zirconia as a solid solution. The sintered body of the present invention has a peak of $2\theta=30\pm2°$ (hereinafter, also referred to as "main peak") in XRD measurement using CuKα ray (λ=0.15418 nm) as a radiation source. The main peak is a peak in which the XRD peak of the tetragonal zirconia (2θ=30.0±2°) and the XRD peak of the cubic zirconia (2θ=29.6±2°) are overlapped and is the XRD peak having the most intense diffraction intensity in the XRD pattern of the sintered body of the present invention. It can be confirmed that the lanthanum is dissolved in zirconia as a solid solution in the sintered body of the present invention because the lattice constant (lattice parameter) determined from the main peak is greater than that of a zirconia sintered body in which no lanthanum is dissolved as a solid solution. For example, when the sintered body of the present invention contains lanthanum and 3 mol % of yttria, the lattice constant thereof becomes greater than the lattice constant of a zirconia sintered body containing only the same amount of yttria. The large lattice constant can be confirmed by the shift of the main peak to the lower angle side in the XRD pattern.

Furthermore, preferably, the sintered body of the present invention substantially contains no complex oxide formed from lanthanum and zirconium or no lanthanum oxide (hereinafter, also referred to as "lanthanum oxide and the like"). Since no lanthanum oxide and the like are contained, the sintered body of the present invention becomes a sintered body having even higher translucency. Absence of the lanthanum oxide and the like can be confirmed by the absence of the corresponding XRD peaks except the XRD peak of the zirconia, in the XRD pattern of the sintered body of the present invention. Examples of the lanthanum oxide and the like include $La_2Zr_2O_7$ and $La_2O_3$.

The lanthanum content of the sintered body of the present invention is preferably 1 mol % or greater. By allowing 2 mol % or greater of lanthanum to be contained, the domain in the crystal grain tends to be fine. Note that the lanthanum content (mol %) is a mole ratio of the lanthanum in terms of oxide amount ($La_2O_3$) to the total of the zirconia, the stabilizer, and the lanthanum in terms of oxide amount in the sintered body. The lanthanum content of the sintered body of the present invention is preferably 10 mol % or less to dissolve all the lanthanum as a solid solution in the zirconia. By setting the content of the lanthanum to be 10 mol % or less, deposition of the lanthanum oxide and the like is further suppressed and the strength of the sintered body of the present invention tends to be high. Examples of the preferred lanthanum content include from 1 mol % to 10 mol %, from 1 mol % to 7 mol %, from 2 mol % to 10 mol %, from 2 mol % to 7 mol %, from 2 mol % to 6.5 mol %, and from 3 mol % to 6.5 mol %.

Although the lanthanum is a lanthanoid element, the sintered body of the present invention preferably contains no lanthanoid element except the lanthanum. Examples of the lanthanoid element except the lanthanum include europium (Eu), gadolinium (Gd), terbium (Tb), dysprosium (Dy), holmium (Ho), erbium (Er), thulium (Tm), ytterbium (Yb), and lutetium (Lu). When the lanthanoid element except the lanthanum is contained, it is difficult to obtain a crystal grain containing the cubic domain and the tetragonal domain. Thus, the lanthanoid element except the lanthanum is preferably not contained in an amount exceeding the amount contained as unavoidable impurities. Although the lanthanoid element except lanthanum of the sintered body of the present invention is preferably not contained, the content of the lanthanoid element except lanthanum in the sintered body of the present invention is, for example, 0.6 mol % or less taking the measurement error of the composition analysis into consideration.

The sintered body of the present invention contains a stabilizer. The stabilizer is dissolved in the zirconia as a solid solution. By dissolving the lanthanum and the stabilizer in zirconia as a solid solution, even in a low temperature environment such as at room temperature, the crystal grain of the sintered body of the present invention contains the cubic domain and the tetragonal domain. The stabilizer is preferably at least one type selected from the group consisting of yttria ($Y_2O_3$), scandia ($Sc_2O_3$), calcia (CaO), magnesia (MgO), and ceria ($CeO_2$). From the perspective of ease in industrial application, the stabilizer is preferably at least one selected from the group consisting of calcia, magnesia, and yttria, and is further preferably yttria.

The amount of the stabilizer contained in the sintered body of the present invention is, for example, from 2 mol % to 7 mol %, from 2 mol % to 5 mol %, from 2.1 mol % to 4.9 mol %, and 2 mol % to 4 mol %. Note that the stabilizer content (mol %) is a mole ratio of the stabilizer to the total of the zirconia, the stabilizer, and the lanthanum in terms of oxide amount ($La_2O_3$) in the sintered body.

The sintered body of the present invention is a zirconia sintered body and is a sintered body containing zirconia as a main component. Thus, the total content of the stabilizer and the lanthanum contained in the sintered body of the present invention needs to be less than 50 mol %. The zirconia content of the sintered body of the present invention needs to be greater than 50 mol %, and is preferably 60 mol % or greater, 80 mol % or greater, 83 mol % or greater, and 90 mol % or greater.

The sintered body of the present invention may contain alumina ($Al_2O_3$). By allowing alumina to be contained, high translucency tends to be achieved, particularly, in a sintered body having high strength. When the sintered body of the present invention contains alumina, the alumina content is preferably from 100 ppm by weight to 2000 ppm by weight, and from 200 ppm by weight to 1000 ppm by weight. Note that the alumina content (ppm by weight) is a weight ratio of the aluminum in terms of oxide amount ($Al_2O_3$) relative to the total weight of the zirconia, the stabilizer, and the lanthanum in terms of oxide amount ($La_2O_3$) in the sintered body.

Although the sintered body of the present invention contains the composition described above, the sintered body may also contain unavoidable impurities. Examples of the unavoidable impurities include rare earth elements (Ce, Pr, Nd, Sm, Eu, Gd, Tb, Dy, Ho, Er, Tm, Yb, and Lu) except hafnium (Hf) and lanthanum.

The following molar compositions are examples of preferable compositions of the sintered body of the present invention.

Zirconia ($ZrO_2$): from 90 mol % to 95 mol %
Stabilizer: from 2 mol % to 5 mol %
Lanthanum ($La_2O_3$): 2 mol % to 6.5 mol %

The following molar compositions are examples of particularly preferable compositions of the sintered body of the present invention.

Zirconia ($ZrO_2$): from 92 mol % to 94 mol %
Stabilizer: from 2 mol % to 4 mol %
Lanthanum ($La_2O_3$): 3 mol % to 5 mol %

The stabilizer in the composition described above is preferably yttria.

The sintered body of the present invention has the cubic domain and the tetragonal domain in the crystal grain. By allowing the cubic domain and the tetragonal domain to be contained in the crystal grain, high strength is achieved as well as high translucency. In the present invention, the domain is at least one of crystallite or aggregate of crystallites in the crystal grain and is a part where the identical crystal structure is continued. Furthermore, the cubic domain is a domain in which the crystal structure is a cubic fluorite structure, and the tetragonal domain is a domain in which the crystal structure is a tetragonal fluorite structure. The sintered body of the present invention having the cubic domain and the tetragonal domain in the crystal grain can be confirmed by the Rietveld analysis of the XRD pattern. That is, by the Rietveld analysis of the XRD pattern, it can be confirmed that the sintered body of the present invention has the cubic phase and the tetragonalphase. Furthermore, since the crystallite size of each of the cubic phase and the tetragonal phase calculated by the Rietveld analysis is smaller than the crystal grain size, it can be confirmed that the cubic domain and the tetragonal domain are contained in the crystal grain. Although the sintered body of the present invention contains the crystal grains having the cubic domain and the tetragonal domain, the sintered body is preferably formed from crystal grains having the cubic domain and the tetragonal domain.

Since the sintered body of the present invention contains the domains described above, the crystal structure thereof contains cubic fluorite structure and tetragonal fluorite structure. Furthermore, preferably, the sintered body of the present invention substantially contains no monoclinic phase. Note that "substantially containing no monoclinicphase" refers to the condition where no XRD peak of monoclinic phase is observed in the XRD pattern.

The lanthanum concentrations in the cubic domain and in the tetragonal domain may be the same. However, in the sintered body of the present invention, the lanthanum concentration of the cubic domain and the lanthanum concentration of the tetragonal domain in the crystal grain may be different. Further, the lanthanum concentration of the cubic domain may be higher than the lanthanum concentration of the tetragonal domain. In the present invention, the lanthanum concentration in each domain can be observed by the composition analysis by transmission electron microscope (hereinafter, referred to as "TEM") observation.

In the sintered body of the present invention, the average crystallite size calculated from the full-width at half maximum of the main peak (hereinafter, referred to as "FWHM") (hereinafter, also simply referred to as "average crystallite size") is preferably 255 nm or less. By setting the average crystallite size to 250 nm or less, 200 nm or less, 150 nm or less, or 130 nm or less, translucency tends to be high. Furthermore, by setting the average crystallite size to 100 nm or less, 60 nm or less, 50 nm or less, or 30 nm or less, light scattering can be further suppressed. As a result, even higher translucency of the sintered body of the present invention can be achieved.

The average crystallite size is preferably small; however, for example, in the sintered body of the present invention, the average crystallite size is typically 2 nm or greater, 5 nm or greater, 10 nm or greater, and 15 nm or greater.

The average crystallite size of the sintered body of the present invention of 255 nm or less can be confirmed by the condition where the FWHM is 0.1536° or greater in the XRD pattern of the sintered body of the present invention. Thus, the FWHM of the sintered body of the present invention is preferably 0.1536° or greater. A greater FWHM leads to a smaller average crystallite size. For example, when the average crystallite size is 250 nm or less, the FWHM is 0.154° or greater. When the average crystallite size is 200 nm or less, the FWHM is 0.1635° or greater. When the average crystallite size is 150 nm or less, the FWHM is 0.178° or greater. When the average crystallite size is 130 nm or less, the FWHM is 0.187° or greater. When the average crystallite size is 100 nm or less, the FWHM is 0.25° or greater. The FWHM is preferably 0.3° or greater, and more preferably 0.4° or greater. On the other hand, as the crystallinity is higher, the FWHM of the XRD peak becomes smaller; however, the FWHM that can be measured by typical XRD measurement is at most approximately 40°. The FWHM of the main peak of the sintered body of the present invention is, for example, 1° or less, and 0.7° or less.

Note that the crystallite size of each of the cubic phase and the tetragonal phase contained in the crystal grain of the present invention can be determined by the Rietveld analysis of the XRD pattern of the sintered body of the present invention. That is, by the Rietveld method, the XRD pattern of the sintered body of the present invention is separated into the XRD peak assigned to the cubic phase and the XRD peak assigned to the tetragonal phase. The FWHM of the XRD peak of each crystal structure after the separation is determined, and then the crystallite size is determined from the obtained FWHM using the following Scherrer equation.

$$D = K \times \lambda / ((\beta - B) \times \cos\theta)$$

In the equation above, D is a crystallite size (nm) of each crystal, K is the Scherrer constant (1.0), $\lambda$ is the wavelength of CuK$\alpha$ (0.15418 nm), $\beta$ is the FWHM (°), B is the instrument constant (0.1177°), and $\theta$ is the diffraction angle (°) of the XRD peak. The XRD peak used during determination of the FWHM is the XRD peak of $2\theta = 30.0 \pm 2°$ for the tetragonal phase and the XRD peak of $2\theta = 29.6 \pm 2°$ for the cubic phase.

The average crystal grain size of the sintered body of the present invention is, for example, from 20 μm to 100 μm, and from 30 μm to 90 μm. By setting the average crystal grain size to be within such a range, a sintered body having high translucency can be obtained. In the present invention, the average crystal grain size can be measured by a planimetric method.

The sintered body of the present invention preferably has a high density. The density varies depending on the amounts of the stabilizer and the lanthanum. Examples of the density of the sintered body of the present invention include from 6.0 g/cm$^3$ to 6.2 g/cm$^3$, and 6.0 g/cm$^3$ to 6.12 g/cm$^3$.

The sintered body of the present invention has high translucency. Thus, the sintered body of the present invention employs a sample thickness of 1 mm and a total light transmittance using illuminant D65 as a radiation source (hereinafter, also simply referred to as "total light transmittance") of 45% or greater. Higher translucency is preferred, and a total light transmittance of 50% or greater is preferred, and of 55% or greater is more preferred. A larger average crystallite size tends to result in higher total light transmittance. For example, when the lanthanum content is 2.5 mol % or greater, the total light transmittance becomes 65% or greater by setting the average crystallite size to be 25 nm or greater.

The translucency of the sintered body of the present invention needs to satisfy the total light transmittance described above. However, when the sample thickness is set to 1 mm, the in-line transmittance using illuminant D65 as a radiation source (hereinafter, also simply referred to as "in-line transmittance") is preferably 1% or greater, 3% or greater, 10% or greater, 20% or greater, and 30% or greater since a sintered body having even higher transparency can be obtained. The upper limit of the in-line transmittance of the sintered body of the present invention is, for example, 70% or less and 66% or less. On the other hand, when the sample thickness of the sintered body of the present invention is set to 1 mm, the defraction transmittance using illuminant D65 as a radiation source (hereinafter, also simply referred to as "defraction transmittance") is preferably 10% or greater, 15% or greater, and 20% or greater. An example of more preferred defraction transmittance is from 30% to 65%.

The sintered body of the present invention has high strength. Examples of the bending strength of the sintered body of the present invention are 500 MPa or greater and 600 MPa or greater. Since a wider range of application is possible, the strength of the sintered body of the present invention is preferably 800 MPa or greater and more preferably 1000 MPa or greater. The strength in the present invention is, for example, in terms of biaxial bending strength measured in accordance with ISO/DIS6872, from 500 MPa to 1600 MPa, and from 600 MPa to 1500 MPa. Furthermore, the strength in the present invention is, for example, in terms of three-point bending strength measured in accordance with JIS R1601, from 500 MPa to 1500 MPa, and from 600 MPa to 1200 MPa.

The sintered body of the present invention preferably has fracture toughness that is equal to or greater than the fracture toughness of translucent zirconia sintered body formed from cubic zirconia, such as 8 mol % yttria-containing zirconia sintered body. As a result, the sintered body of the present invention can be used as a member composed of conventional translucent zirconia sintered body. The fracture toughness of the sintered body of the present invention is, for example, 1.7 MPa·m$^{0.5}$ or greater, 1.8 MPa·m$^{0.5}$ or greater, 2 MPa·m$^{0.5}$ or greater, and 2.2 MPa·m$^{0.5}$ or greater.

In the present invention, the fracture toughness can be measured by IF method or SEPB method in accordance with JIS R 1607.

Next, the method for manufacturing the zirconia sintered body of the present invention will be described.

The zirconia sintered body of the present invention can be manufactured by a manufacturing method including: a mixing step of obtaining a mixed powder by mixing a zirconia source, a stabilizer source, and a lanthanum source; a molding step of obtaining a green body by molding the obtained mixed powder; a sintering step of obtaining a sintered body by sintering the obtained green body at a sintering temperature of 1650° C. or higher; and a temperature lowering step of lowering the temperature from the sintering temperature to 1000° C. at a temperature lowering rate exceeding 1° C./min.

In the mixing step, a mixed powder is obtained by mixing a zirconia source, a stabilizer source, and a lanthanum source. The mixing method may be wet mixing or dry mixing as long as the zirconia source, the stabilizer source, and the lanthanum source are mixed uniformly. Since even more uniform mixed powder can be obtained, the mixing method is preferably wet mixing, and more preferably wet mixing by at least one of wet ball mill or wet stirring mill.

The zirconia source is zirconia or a precursor thereof, and an example thereof includes zirconia powder having a BET specific surface area of 4 to 20 m$^2$/g.

Examples of the stabilizer source include powder of at least one type selected from the group consisting of yttria, scandia, calcia, magnesia, and ceria (stabilizer) or a precursor thereof. Furthermore, yttria powder or a precursor thereof can be exemplified.

Furthermore, the zirconia source is preferably a zirconia powder containing a stabilizer. Such a zirconia powder serves as a zirconia source and a stabilizer source. The stabilizer contained in the zirconia powder is preferably at least one type selected from the group consisting of yttria, scandia, calcia, magnesia, and ceria, and is more preferably yttria. As the stabilizer-containing zirconia powder, a zirconia powder containing from 2 mol % to 7 mol % of a stabilizer is preferred, and a zirconia powder having the BET specific surface area of 4 to 20 m$^2$/g and containing from 2 mol % to 7 mol % of a stabilizer is more preferred. The amount of the stabilizer contained in the stabilizer-containing zirconia powder is preferably from 2 mol % to 5 mol %, and more preferably from 2 mol % to 4 mol %.

Examples of the lanthanum source include compounds containing lanthanum, and examples thereof include at least one type of lanthanum oxide, lanthanum hydroxide, lanthanum nitrate, lanthanum sulfate, lanthanum chloride, lanthanum carbonate, and pyrochlore $La_2Zr_2O_7$. At least one of lanthanum oxide and $La_2Zr_2O_7$ is preferred.

The mixed powder may contain an alumina source. Examples of the alumina source include compounds containing aluminum, and examples thereof include at least one type selected from the group consisting of alumina, aluminum hydroxide, aluminum carbonate, and spinel. In particular, alumina is exemplified. Examples of preferred alumina include at least α-alumina or γ-alumina. In particular, α-alumina is exemplified.

The composition of the mixed powder may have desired proportions; however, the composition of the mixed powder includes greater than 83 mol % but 97 mol % or less of zirconia, from 2 mol % to 7 mol % of a stabilizer, and from 1 mol % to 10 mol % of lanthanum, in terms of oxide amount.

The following molar compositions are examples of preferable compositions of the mixed powder.
Zirconia ($ZrO_2$): from 90 mol % to 95 mol %
Stabilizer: from 2 mol % to 5 mol %
Lanthanum ($La_2O_3$): 2 mol % to 6.5 mol %

The following molar compositions are examples of particularly preferable compositions of the mixed powder.
Zirconia ($ZrO_2$): from 92 mol % to 94 mol %
Stabilizer: from 2 mol % to 4 mol %
Lanthanum ($La_2O_3$): 3 mol % to 5 mol %

The stabilizer in the composition described above is preferably yttria.

In the molding step, a green body is obtained by molding the mixed powder. As long as a green body having a desired shape can be obtained, any molding method can be employed. Examples of the molding method include at least one type selected from the group consisting of press molding, injection molding, sheet molding, extrusion molding, and casting, and the molding method is preferably press molding or injection molding.

Furthermore, the obtained green body may have any shape, and examples thereof include shapes such as disk-like, cylindrical, and polyhedral shapes, orthodontic brackets, jigs for semiconductor manufacturing, and other complex shapes.

In the sintering step, by sintering the green body, a sintered body having a crystal structure that is a high-temperature crystal structure such as cubic is obtained. For this, in the sintering step, the obtained green body is sintered at a sintering temperature of 1650° C. or higher. By sintering at 1650° C. or higher, the crystal structure of the sintered body is expected to become a high-temperature crystal structure. By subjecting the sintered body having a high-temperature crystal structure to a temperature lowering step, the crystal structure in the crystal grain forms the cubic domain and the tetragonal domain, thereby obtaining a sintered body having a crystal structure of the sintered body of the present invention. The sintering temperature is preferably 1700° C. or higher, more preferably 1725° C. or higher, and even more preferably 1750° C. or higher. When a general purpose kiln is used, the sintering temperature is, for example, 2000° C. or lower, 1900° C. or lower, or 1800° C. or lower.

Any sintering method can be employed as long as the sintering is performed at the sintering temperature described above. Examples of the sintering method include at least one selected from the group consisting of pressureless sintering, pressure sintering, and vacuum sintering, and pressureless sintering and pressure sintering is preferred.

In the manufacturing method of the present invention, examples of the preferred sintering step include a sintering method in which only pressureless sintering is performed (hereinafter, also referred to as "one-step sintering method") or a sintering step including a primary sintering to obtain a primary sintered body by sintering the green body at 1000° C. or higher but lower than 1650° C. and a secondary sintering of sintering the primary sintered body at 1650° C. or higher (hereinafter, also referred to as "two-step sintering method").

With the one-step sintering method, the sintered body of the present invention needs to be obtained by employing pressureless sintering for the sintering step. Pressureless sintering is a method of sintering by simply heating without applying any external force to the green body during the sintering. In the pressureless sintering, the green body obtained in the molding step needs to be subjected to pressureless sintering to obtain a sintered body. The sintering temperature needs to be 1600° C. or higher, and is preferably from 1700° C. to 1900° C. The sintering atmosphere may be any of an oxidizing atmosphere or a reducing atmosphere. For convenience, an air atmosphere is preferred.

The two-step sintering method subjects the primary sintered body, which is obtained by subjecting the green body to primary sintering, to secondary sintering. In the primary sintering, the green body is preferably sintered at 1000° C. or higher but lower than 1650° C. The atmosphere in the primary sintering is preferably an oxidizing atmosphere or a reducing atmosphere, and an air atmosphere is preferred. Preferable primary sintering is, for example, a pressureless sintering at 1000° C. or higher but lower than 1650° C., or 1400° C. or higher but 1520° C. or lower, in the air. By this, the structure of the obtained primary sintered body becomes fine. In addition, pores are less likely to be generated in the crystal grain of the primary sintered body.

In the secondary sintering, the primary sintered body is sintered at 1650° C. or higher, 1700° C. or higher, 1725° C. or higher, or 1750° C. or higher. To obtain a sintered body having high strength, the secondary sintering temperature is preferably 2000° C. or lower, 1900° C. or lower, or 1800° C. or lower. By setting the secondary sintering temperature to be 2000° C. or lower, coarse crystal grains are less likely to be formed.

To obtain a sintered body having higher density, the secondary sintering is preferably hot isostatic pressing (hereinafter, referred to as "HIP") treatment.

The time of HIP treatment (hereinafter, referred to as "HIP time") is preferably at least 10 minutes. When the HIP time is at least 10 minutes, pores of the sintered body is sufficiently removed during the HIP treatment.

The pressure medium of the HIP treatment (hereinafter, also simply referred to as "pressure medium") is exemplified by an argon gas, a nitrogen gas, and oxygen; however, ordinary argon gas is convenient.

The pressure of the HIP treatment (hereinafter, also referred to as "HIP pressure") is preferably 5 MPa or higher, and more preferably 50 MPa or higher. By setting the HIP pressure to be 5 MPa or higher, removal of the pores in the sintered body is promoted. The upper limit of the pressure is not particularly limited; however, when an ordinary HIP device is used, the HIP pressure is 200 MPa or lower.

In the HIP treatment, the green body or the primary sintered body is preferably placed in a container formed from a nonreducible material. By this, local reduction of the sintered body due to a reducing component derived from the material of the HIP device, such as a heating element, is suppressed. Examples of the nonreducible material include at least one type selected from the group consisting of alumina, zirconia, mullite, yttria, spinel, magnesia, silicon nitride, and boron nitride, and in particular, at least one of alumina and zirconia can be exemplified.

In the temperature lowering step, the temperature is lowered from the sintering temperature to 1000° C. at a temperature lowering rate exceeding 1° C./min. A sintered body having high translucency can be obtained by setting the temperature lowering rate to higher than 1° C./min, 5° C./min or higher, or 8° C. or higher. When the temperature lowering rate is 1° C./min or lower, translucency of the obtained sintered body is lowered since deposition and/or monoclinic phase are generated. As a result, the translucency of the obtained sintered body becomes significantly low. To obtain a lanthanum-dissolved zirconia sintered body having higher translucency, the temperature lowering from the sintering temperature to 1000° C. is preferably performed at the temperature lowering rate of 10° C./min or higher, 15° C./min or higher, 30° C./min or higher, or 50° C./min or higher.

The manufacturing method of the present invention may include an annealing step in which the sintered body after the temperature lowering step is heat-treated. By subjecting the sintered body to the annealing step, even higher translucency of the sintered body may be achieved. In the annealing step, the sintered body is treated in an oxidizing atmosphere at 900° C. to 1200° C., or 980° C. to 1030° C.

Advantageous Effects of Invention

The present invention can provide a zirconia sintered body having both high translucency and high strength. The sintered body of the present invention has higher translucency and higher mechanical strength compared to those of conventional translucent ceramics. Thus, when the sintered body is used as a dental component that requires aesthetic quality, such as orthodontic bracket, the size thereof can be made small. Thus, the sintered body can be used as a dental component having higher aesthetic quality.

EXAMPLES

Figure 1:
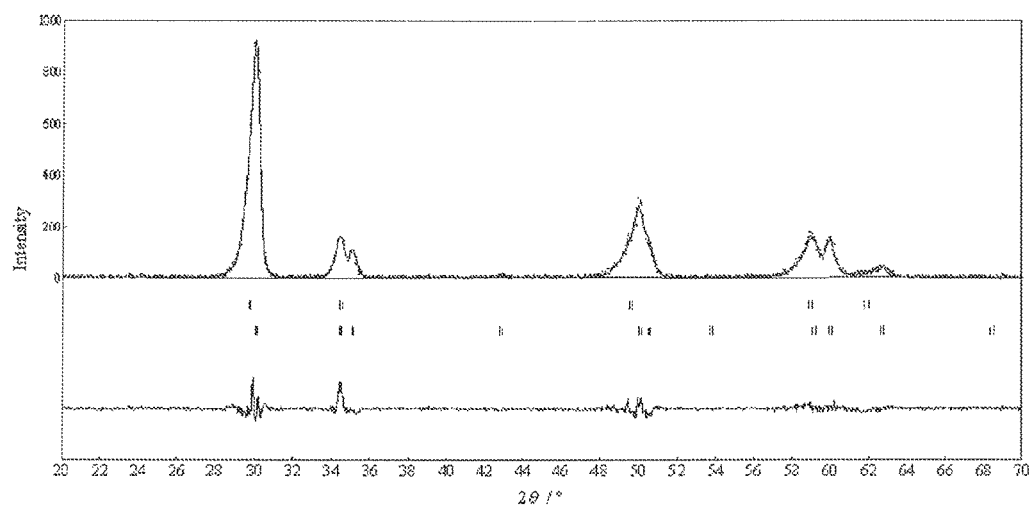
FIG. 1 is the Rietveld analysis result of the XRD pattern of the zirconia sintered body of Example 1.

The present invention will be described specifically with reference to examples and comparative examples hereinafter. However, the present invention is not limited to the examples.

Measurement of Density

The measured density of a sintered body sample was determined through an underwater weight measurement conducted by the Archimedes method.

Measurement of Average Crystal Grain Size

After the sintered body sample was surface-ground, mirror-polishing was performed by using 9 μm, 6 μm, and 1 μm diamond abrasive grains in this order. The polished surface was maintained at 1400° C. for 1 hour and thermally etched, and then the polished surface was observed by SEM. From the obtained SEM observation image, the average crystal grain size was determined by a planimetric method.

Identification of Crystal Structure

By subjecting the XRD pattern obtained by the XRD measurement of the sintered body sample to identification analysis, crystal structure of each sintered body sample was identified, and the presence of impurity layer was confirmed. The XRD measurement was performed for the sintered body sample which had undergone mirror-polishing by using an ordinary powder X-ray diffraction instrument (instrument name: Ultima III, manufactured by Rigaku Corporation). The XRD measurement conditions were as follows.

Radiation source: CuKα ray ($\lambda$=0.15418 nm)
Measurement mode: step scan
Scanning condition: 0.04°/sec
Divergence slit: 0.5 deg
Scattering slit: 0.5 deg
Receiving slit: 0.3 mm
Measurement time: 1.0 sec
Measurement range: $2\theta$=20° to 80°

For the identification analysis of the XRD pattern, an XRD analysis software (trade name: JADE 7, manufactured by MID) was used.

Measurement of Average Crystallite Size

The average crystallite size of the sintered body sample was determined using the Scherrer equation for the range of $2\theta$=27° to 30° of the XRD pattern obtained by the same measurement method that was conducted for the identification of crystal phase.

$$D = K \times \lambda / ((\beta - B) \times \cos \theta)$$

In the equation above, D is the average crystallite size (nm), K is the Scherrer constant (1.0), $\lambda$ is the wavelength of CuKα (0.15418 nm), $\beta$ is the FWHM (°), B is the instrument constant (0.1177°), and $\theta$ is the diffraction angle (°) of the main peak.

Note that the main peak used the peak assigned to the (111) plane of the cubic phase and the peak assigned to the (111) plane of the tetragonal phase of the zirconia, which were overlapped, as a single peak.

Furthermore, the FWHM was determined using the Integral Analysis for Windows (Version 6.0), manufactured by Rigaku Corporation.

Rietveld Analysis

By subjecting the obtained XRD pattern by Rietveld analysis by the same measurement method that was conducted for the identification of crystal structure, the lattice constant, the crystallite size, and the proportion of each crystal structure of cubic phase and tetragonal phase in the sintered body sample were determined. A general purpose program (Rietan-2000) was used for the Rietveld analysis.

From the obtained lattice constant, the $Y_2O_3$ concentration in the tetragonal phase was determined based on the following equations.

$$YO_{1.5} = (1.0223 - cf/af)/0.001319$$

$$Y_2O_3 = 100 \times YO_{1.5}/(200 - YO_{1.5})$$

In the equations described above, $YO_{1.5}$ is the yttria concentration, cf and af are respectively the lattice constant of the c-axis and the lattice constant of the a-axis of the tetragonal fluorite structure determined by the Rietveld analysis.

Measurement of Transmittance

The total light transmittance (hereinafter, referred to as "TT"), defraction transmittance (hereinafter, referred to as "DF"), and in-line transmittance (hereinafter, referred to as "PT") of the sample were measured by the method in accordance with the method of JIS K321-1. The optical transmittance was measured by irradiating the measurement sample with the standard light D65 and by detecting the light flux transmitted through the measurement sample using an integrating sphere. An ordinary haze meter (instrument name: Haze Meter NDH 2000, manufactured by Nippon Denshoku Industries Co., Ltd.) was used for the measurement.

For the measurement sample, a disk-like green body having a diameter of 16 mm and a thickness of 1.0 mm was used. Prior to the measurement, the both surfaces of the measurement sample were mirror-polished until the surface roughness Ra became 0.02 μm or less.

Measurement of Wavelength Dependency of Transmittance

As the wavelength dependency of transmittance of the sintered body sample, the spectral total transmittance (hereinafter, referred to as "S-TT") and the spectral in-line transmittance (hereinafter, referred to as "S-PT") were measured by UV-Vis. The measurement conditions were as follows.

Light source: Deuterium lamp and halogen lamp
Measurement wavelength: 200 to 800 nm
Measurement step: 1 nm For the UV-Vis measurement, an ordinary double beam spectrophotometer (instrument name: V-650, manufactured by JASCO Corporation) was used.

For the measurement sample, a disk-like green body having a diameter of 16 mm and a thickness of 1.0 mm was used. Prior to the measurement, the both surfaces of the measurement sample were mirror-polished until the surface roughness Ra became 0.02 μm or less.

Measurement of Angular Distribution of Transmitted Light

The angular distribution of transmitted light was measured using goniophotometer (instrument name: GP-200, manufactured by Murakami Color Research Laboratory Co., Ltd.). For the measurement sample, a disk-like green body having a diameter of 16 mm and a thickness of 1.0 mm was used. Prior to the measurement, the both surfaces of the measurement sample were mirror-polished until the surface roughness Ra became 0.02 μm or less.

Observation of Element Distribution

The element distribution in the crystal grain was measured by TEM observation. Prior to the measurement, the sample was processed into a thin piece by a focused ion beam (FIB). After the processing, the thin piece was subjected to ion milling finishing and carbon deposition to form a measurement sample. The TEM observation was performed by using an ordinary TEM (instrument name: EM-2000FX, manufactured by JEOL Ltd.) at an acceleration voltage of 200 kV.

Measurement of Biaxial Bending Strength

The biaxial bending strength of the sample was measured by biaxial bending strength measurement in accordance with ISO/DIS 6872. The measurement was performed for the measurement sample in which the both surfaces were mirror-polished and which had a thickness of 1 mm.

Measurement of Three-Point Bending Strength

The three-point bending strength of the sample was measured by a method in accordance with JIS R 1601 "Testing method for flexural strength of fine ceramics". For the measurement sample, a sample which was mirror-polished until the surface roughness Ra became 0.02 μm or less was used. Furthermore, five measurements of the strength were performed for one sample, and the average value thereof was used as the three-point bending strength.

Measurement of Fracture Toughness

The fracture toughness of the sample was measured by the IF method and the SEPB method in accordance with JIS R 1607. For the measurement sample, a sample which was mirror-polished until the surface roughness Ra became 0.02 μm or less was used. Five measurements were performed for one sample, and the average value thereof was used as the fracture toughness of the sample. The measurement conditions in the IF method were as follows.
Indentation load: 5 kgf
Elastic modulus of sintered body: 205 GPa The fracture toughness obtained by the IF method was recorded as $K_{IC}$(IF) and the fracture toughness obtained by the SEPB method was recorded as $K_{IC}$(SEPB).

Hydrothermal Degradation Test

The sintered body sample was treated in a hot water atmosphere, and degradation evaluation was performed. Pure water and the sintered body sample were placed in a pressure-resistant container made of stainless steel and maintained at 140° C. for 24 hours to perform the hydrothermal degradation test. After the maintenance, the collected sintered body sample was subjected to XRD measurement. The proportion of the XRD peak assigned to the monoclinic phase contained in the obtained XRD pattern was determined based on the following equation, and the volume fraction of the monoclinic phase in the sintered body sample (hereinafter, also referred to as "monoclinic phase fraction") was determined.

$$X=(Im(111)+Im(11-1))/(Im(111)+Im(11-1)+It(111)+Ic(111))$$

Note that X is the monoclinic phase fraction of the sample, Im(111) is the XRD peak intensity assigned to the (111) plane of the monoclinic phase, Im(11-1) is the XRD peak intensity assigned to the (11-1) plane of the monoclinic phase, It(111) is the XRD peak intensity assigned to the (111) plane of the tetragonal, and Ic(111) is the XRD peak intensity assigned to the (111) plane of the cubic.

Measurement of Thermal Conductivity

The thermal conductivity of the sintered body sample was measured by the laser flash method. For the measurement, a laser flash method thermal constant measurement system (instrument name: TC-1200RH, manufactured by Advance Riko, Inc.) was used.

Synthesis Example (Synthesis of $La_2Zr_2O_7$ Powder)

An $La_2Zr_2O_7$ powder was synthesized by a solid-phase method. That is, a mixed powder was obtained by mixing zirconium oxide (trade name: TZ-0Y, manufactured by Tosoh Corporation) and lanthanum oxide (purity: 99.99%; manufactured by Wako Pure Chemical Industries, Ltd.). The mixing was performed by wet mixing in an ethanol solvent using a ball mill with zirconia balls having a diameter of 10 mm.

The mixed powder after the mixing was dried or calcined to obtain a calcined powder. As the calcining condition, heat treatment was performed in atmosphere at 1100° C. for 10 hours. The obtained calcined powder was wet mixed in the same conditions as those of the mixing described above and then dried. The powder after the drying was sintered in the air at 1400° C. for 2 hours to obtain a white powder, and this was used as the $La_2Zr_2O$ powder (hereinafter, also referred to as "LZO powder").

By XRD measurement, it was confirmed that the obtained white powder was an $La_2Zr_2O_7$ monophase.

Example 1

The LZO powder was added to a 3 mol % yttria-containing zirconia powder having a BET specific surface area of 7 m²/g (trade name: TZ-3YS, manufactured by Tosoh Corporation) in a manner that the weight ratio of the LZO powder to the zirconia powder was 20 wt. %, and mixed to obtain a mixed powder. The mixing was performed by wet mixing in an ethanol solvent for 120 hours using a ball mill with zirconia balls having a diameter of 10 mm. The obtained mixed powder was dried in the air at 80° C. to form a source powder.

The source powder was molded by uniaxial pressing by mold pressing to obtain a pregreen body. The pressure of the uniaxial pressing was 50 MPa. The obtained pregreen body was subjected to cold isostatic pressing (hereinafter, referred to as "CIP") treatment to obtain a cylindrical green body having a diameter of 20 mm and a thickness of approximately 3 mm. The pressure of the CIP treatment was 200 MPa.

The green body was subjected to primary sintering in the air, at a temperature elevation rate of 100° C./h, a sintering temperature of 1450° C., and for a sintering time of 2 hours to obtain a primary sintered body.

The obtained primary sintered body was placed in a container that was made of zirconia and that had a lid, and subjected to HIP treatment to obtain an HIP-treated body. The HIP-treated body was used as the zirconia sintered body of the present example. The HIP treatment conditions were as follows: in a 99.9% argon gas atmosphere as a pressure medium, temperature elevation rate of 600° C./h, HIP temperature of 1750° C., HIP pressure of 150 MPa, and maintaining time for 1 hour.

After the HIP treatment, an HIP-treated body was obtained by lowering the temperature from the sintering temperature to room temperature. Note that the temperature lowering rate from the HIP temperature to 1000° C. was 83° C./min.

The obtained HIP-treated body was subjected to heat treatment in the air at 1000° C. for 1 hour to obtain a colorless translucent sintered body.

Figure 2:
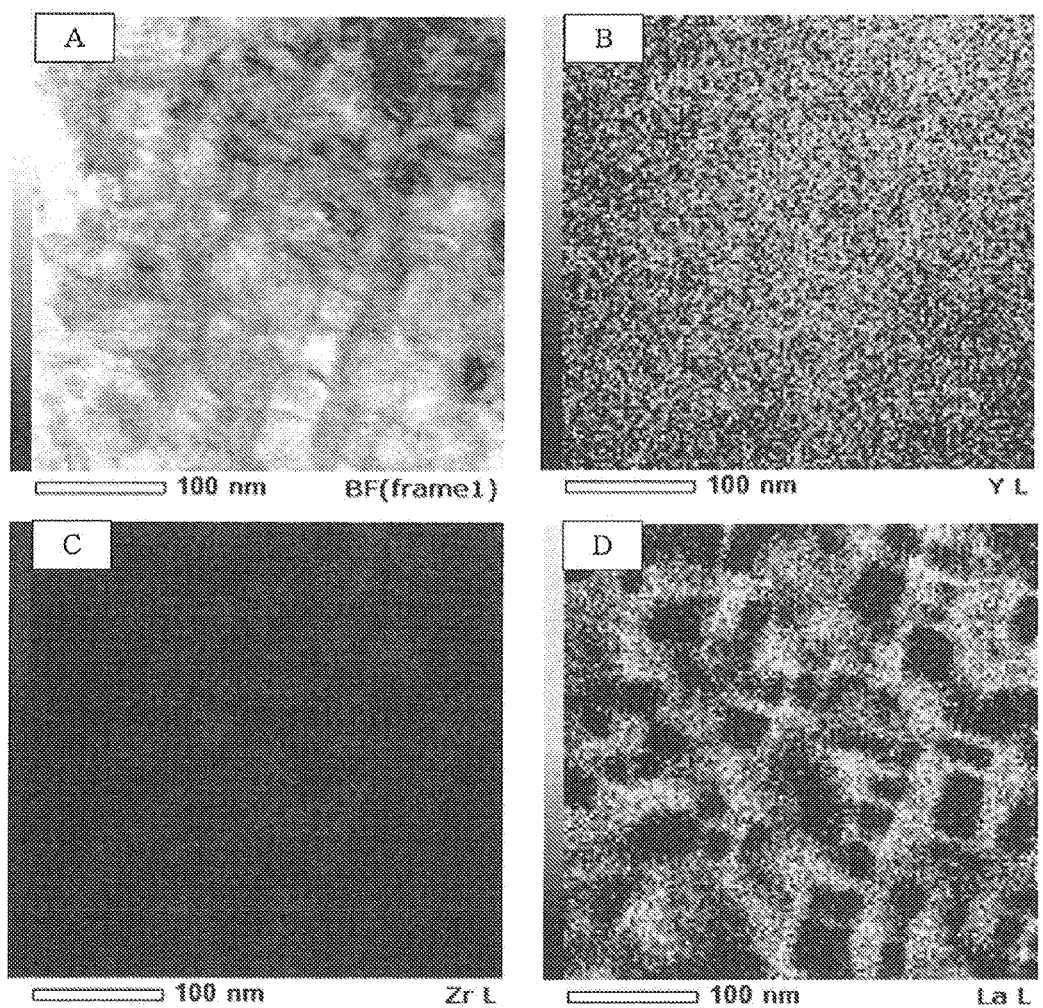
FIGS. 2A to 2D are the TEM observation images of the zirconia sintered body of Example 1 (scale in the views are 100 nm), where A) is the light view image, B) is the element mapping of yttrium, C) is the element mapping of zirconium, and D) is the element mapping of lanthanum.
Figure 3:
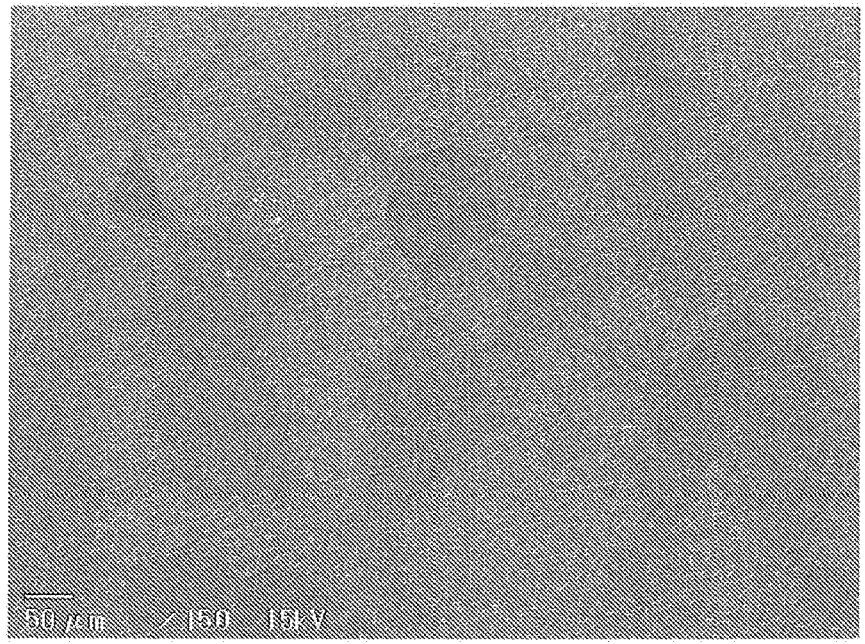
FIG. 3 is the SEM observation image of the zirconia sintered body of Example 1 (scale in the view is 50 μm).

The Rietveld analysis result of the zirconia sintered body of the present example is shown in FIG. 1, the TEM observation images are shown in FIGS. 2A to 2D, and the SEM observation image is shown in FIG. 3. By the XRD pattern of FIG. 1, it was confirmed that the zirconia sintered body of the present example did not contain lanthanum oxide and the like. Furthermore, Table 1 shows the composition analysis results of the crystal grain inner portion and the crystal grain boundary by SEM-EDS. Note that the analysis by the SEM-EDS was performed without subjecting the sintered body to thermal etching treatment. From the Table 1, it was confirmed that the inner portion of the crystal grain and the crystal boundary of the sintered body of the present example did not have different compositions and the sintered body of the present example was a uniform sintered body since the average compositions of the inner portion of the crystal grain and the portion close to the crystal boundary were similar.

TABLE 1

| Detected element | Concentration in inner portion of crystal grain (mol %) | Concentration at crystal grain boundary (mol %) |
|---|---|---|
| Oxygen (O) | 60.3 | 60.1 |
| Yttrium (Y) | 2.2 | 2.7 |
| Zirconium (Zr) | 34.9 | 34.8 |
| Lanthanum (La) | 2.7 | 2.4 |

Furthermore, from FIG. 2A, the cubic domain and the tetragonal domain were confirmed. The domain was approximately 50 nm while the average crystal grain size was 88.3 μm, and it was confirmed that the domain was smaller than the crystal grain size. By this, it was confirmed that the zirconia sintered body of the present example contained the tetragonal domain and the cubic domain in the crystal grain.

Note that, by the Rietveld analysis, it was confirmed that 48.4 wt. % was the cubic phase and 51.6 wt. % was the tetragonal phase in the zirconia sintered body of the present example, the lattice constant of the cubic phase was a=0.51872 nm, the lattice constant of the tetragonal phase was af=0.50975 nm and cf=0.51917 nm, the crystallite size of the cubic phase was 21 nm, and the crystallite size of the tetragonal phase was 32 nm. Note that, in the Rietveld analysis, the reliability factor was Rwp=20% and S=1.28. The $Y_2O_3$ concentration of the tetragonal phase determined from the lattice constant was 1.48 mol %.

Furthermore, from the element mapping by the TEM observation, it was confirmed that the region where lanthanum was present and the region where lanthanum was almost absent (FIG. 2D). From the Rietveld analysis results and the element mapping, it was conceived that the region where lanthanum was present was the region of the cubic phase where the lanthanum was dissolved as a solid solution, and on the other hand, the region where lanthanum was absent was the region of the tetragonal phase. By this, it was confirmed that, in the sintered body of the present example, the lanthanum concentration was higher in the cubic domain than the tetragonal domain.

The sizes of the cubic domain and the tetragonal domain obtained by the TEM observation were the same as the average crystallite size and as each of the crystallite sizes of the tetragonal phase and the cubic phase obtained by the Rietveld analysis. From these results, it was confirmed that, in the sintered body of the present example, the cubic domain was the crystallite of cubic phase and that the tetragonal domain was the crystallite of tetragonal phase.

Figure 4:
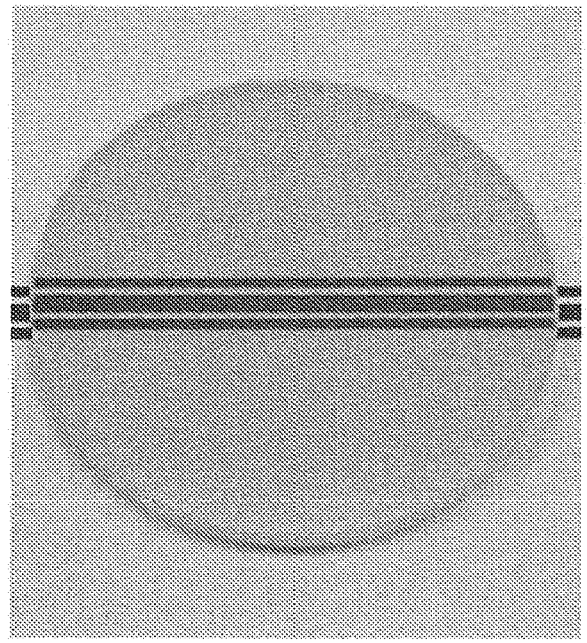
FIG. 4 is the appearance of the zirconia sintered body of Example 1.
Figure 5:
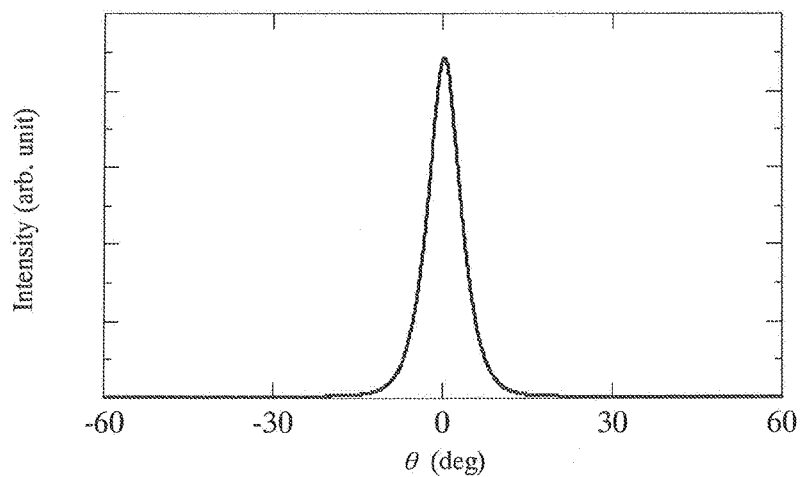
FIG. 5 is the spectrum obtained by goniophotometer of the zirconia sintered body of Example 1.
Figure 6:
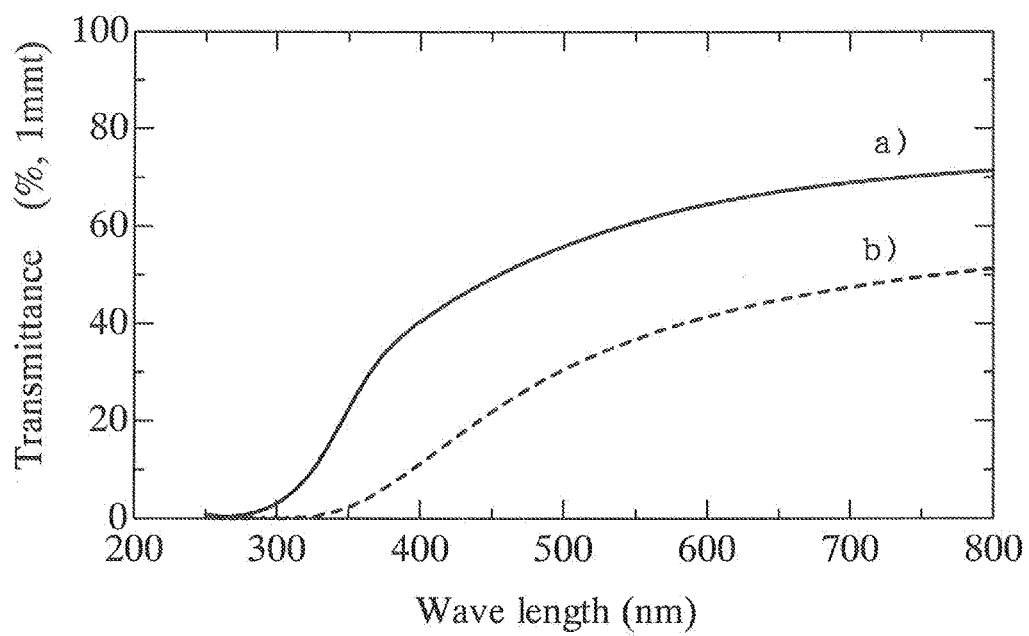
FIG. 6 is the UV-vis spectrum of the zirconia sintered body of Example 1, where a) is the total light transmittance and b) is the in-line transmittance.

FIG. 4 shows the general image of the zirconia sintered body of the present example, FIG. 5 shows the spectrum obtained by goniophotometer, and FIG. 6 shows the UV-Vis spectrum. From FIG. 4, the line on the back surface was observed through the zirconia sintered body of the present example, and thus it was confirmed that the zirconia sintered body of the present invention had translucency. Furthermore, although the defraction transmittance (DF) of the zirconia sintered body of the present example was 24.28%, from FIGS. 5 and 6, it was confirmed that the most of it was the defraction transmittance at angles close to the in-line transmitted light, and has high transmittance in the in-line direction. Furthermore, it was also confirmed that high translucency was achieved in the wavelength range of visible light of 300 nm to 800 nm. By this, it was confirmed that even higher transparency was achieved by the zirconia sintered body of the present invention.

Figure 7:
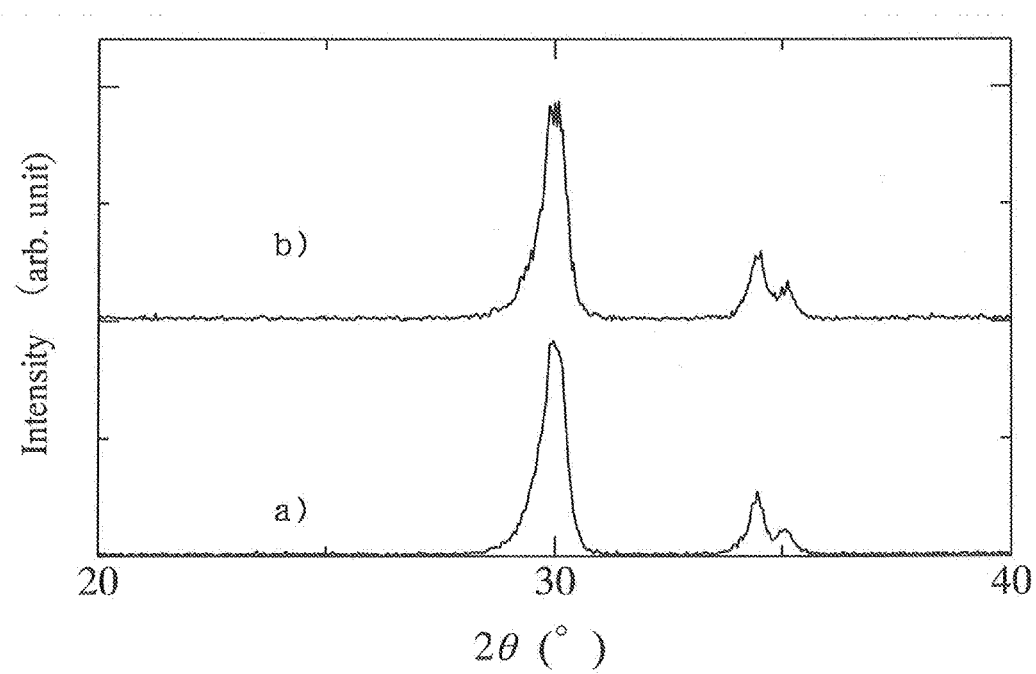
FIG. 7 is the XRD patterns of the zirconia sintered body of Example 1 before and after the hydrothermal degradation test, where a) is prior to the hydrothermal degradation test and b) is after the hydrothermal degradation test.

Furthermore, the monoclinic phase fraction after the hydrothermal degradation test was 0%, and it was confirmed that the zirconia sintered body of the present example was less likely to deteriorate. FIG. 7 shows the XRD pattern after the hydrothermal degradation test.

The evaluation results of the zirconia sintered body of the present example are shown in Table 2.

Example 2

A zirconia sintered body of the present example was obtained by the same method as in Example 1 except for changing the HIP treatment temperature to 1700° C. The evaluation results of the zirconia sintered body of the present example are shown in Table 2.

Example 3

A zirconia sintered body of the present example was obtained by the same method as in Example 1 except for changing the HIP treatment temperature to 1800° C. The evaluation results of the zirconia sintered body of the present example are shown in Table 2.

Example 4

A zirconia sintered body of the present example was obtained by the same method as in Example 1 except for changing the HIP treatment pressure to 54 MPa. The evaluation results of the zirconia sintered body of the present example are shown in Table 2.

Example 5

A zirconia sintered body of the present example was obtained by the same method as in Example 1 except for changing the HIP treatment time to 15 minutes. The evaluation results of the zirconia sintered body of the present example are shown in Table 2.

Example 6

A zirconia sintered body of the present example was obtained by the same method as in Example 1 except for changing the primary sintering temperature to 1425° C. The evaluation results of the zirconia sintered body of the present example are shown in Table 2.

Example 7

A zirconia sintered body of the present example was obtained by the same method as in Example 1 except for adding the LZO powder to the zirconia powder in a manner that the weight ratio of the LZO powder was 15 wt. %. The average crystal grain size of the zirconia sintered body of the present example was 82.1 µm. The evaluation results are shown in Table 2.

Example 8

A zirconia sintered body of the present example was obtained by the same method as in Example 1 except for adding the LZO powder to the zirconia powder in a manner that the weight ratio of the LZO powder was 17.5 wt. % and changing the HIP treatment temperature to 1700° C. The average crystal grain size of the zirconia sintered body of the present example was 48.2 µm. The evaluation results are shown in Table 2.

Example 9

A zirconia sintered body of the present example was obtained by the same method as in Example 1 except for adding the LZO powder to the zirconia powder in a manner that the weight ratio of the LZO powder was 17.5 wt. %, changing the primary sintering temperature to 1500° C., and changing the HIP treatment pressure to 15 MPa. The evaluation results of the zirconia sintered body of the present example are shown in Table 2.

Example 10

A zirconia sintered body of the present example was obtained by the same method as in Example 1 except for adding the LZO powder to the zirconia powder in a manner that the weight ratio of the LZO powder was 25 wt. % and changing the HIP treatment temperature to 1700° C. The average crystal grain size of the zirconia sintered body of the present example was 45.6 µm. The evaluation results are shown in Table 2.

Example 11

A zirconia sintered body of the present example was obtained by the same method as in Example 1 except for adding the LZO powder to the zirconia powder in a manner that the weight ratio of the LZO powder was 17.5 wt. % and changing the HIP treatment temperature to 1725° C. The average crystal grain size of the zirconia sintered body of the present example was 61.2 µm. The evaluation results are shown in Table 2.

Furthermore, Raman analysis was performed for the polished surface and the fracture surface of the test sample after the biaxial bending strength evaluation. The Raman analysis was performed by an ordinary microscopic Raman instrument (instrument name: NRS-5100, manufactured by JASCO Corporation) using a measurement laser wavelength of 532 nm. The obtained Raman spectrum is shown in FIG. 8.

Figure 8:
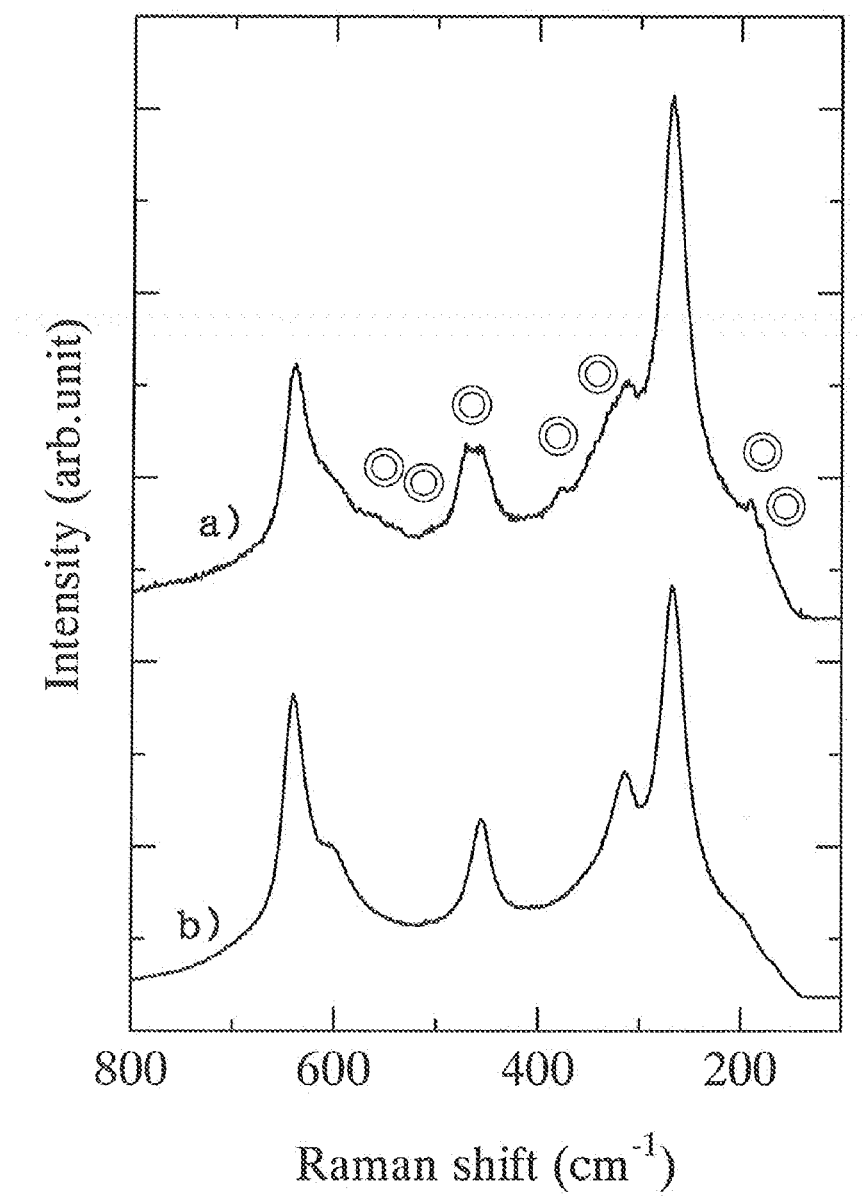
FIG. 8 is the Raman spectrum of the zirconia sintered body of Example 11, where a) shows the fracture surface and b) shows the surface.

From the Raman spectrum of the polishing surface of FIG. 8, peaks other than the peaks assigned to the tetragonal phase and the cubic phase were not observed in the zirconia sintered body of the present example. On the other hand, in addition to the peaks assigned to the tetragonal phase and the cubic phase, peaks assigned to monoclinic phase (550 $cm^{-1}$, 500 $cm^{-1}$, 470 $cm^{-1}$, 380 $cm^{-1}$, 190 $cm^{-1}$, and 180 $cm^{-1}$) were observed in the fracture surface.

By this, it was confirmed that higher strength was achieved in the zirconia sintered body of the present example since the tetragonal phase was subjected to transition into the monoclinic phase in the bending test.

Example 12

A zirconia sintered body of the present example was obtained by the same method as in Example 1 except for adding the LZO powder to the zirconia powder in a manner that the weight ratio of the LZO powder was 25 wt. % and changing the HIP treatment temperature to 1725° C. The average crystal grain size of the zirconia sintered body of the present example was 67.2 µm. The evaluation results are shown in Table 2.

Example 13

A zirconia sintered body of the present example was obtained by the same method as in Example 1 except for using a 3 mol % yttria-containing zirconia powder having a specific surface area of 14 $m^2/g$ (trade name: TZ-3Y, manufactured by Tosoh Corporation) as a zirconia powder, using an $La_2O_3$ powder (purity: 99.99%, manufactured by Wako Pure Chemical Industries, Ltd.) in place of the LZO powder, and adding the $La_2O_3$ powder to the zirconia powder in a manner that the weight ratio of the $La_2O_3$ powder was 10 wt. %. The average crystal grain size of the zirconia sintered body of the present example was 46.9 µm. The evaluation results are shown in Table 2.

Example 14

A zirconia sintered body of the present example was obtained by the same method as in Example 1 except for using an $La_2O_3$ powder (purity: 99.99%, manufactured by Wako Pure Chemical Industries, Ltd.) in place of the LZO powder, adding the $La_2O_3$ powder to the zirconia powder in a manner that the weight ratio of the $La_2O_3$ powder was 10 wt. %, and changing the HIP treatment time to 15 minutes. The average crystal grain size was 33.0 µm. The evaluation results are shown in Table 2.

Example 15

A zirconia sintered body of the present example was obtained by the same method as in Example 1 except for using an La₂O₃ powder (purity: 99.99%, manufactured by Wako Pure Chemical Industries, Ltd.) in place of the LZO powder, adding the La₂O₃ powder to the zirconia powder in a manner that the weight ratio of the La₂O₃ powder was 7.5 wt. %, and changing the HIP treatment temperature to 1725° C. The average crystal grain size of the zirconia sintered body of the present example was 85.3 μm. The evaluation results are shown in Table 2.

Example 16

A zirconia sintered body of the present example was obtained by the same method as in Example 1 except for using an La₂O₃ powder (purity: 99.99%, manufactured by Wako Pure Chemical Industries, Ltd.) in place of the LZO powder, adding the La₂O₃ powder to the zirconia powder in a manner that the weight ratio of the La₂O₃ powder was 7.5 wt. %, and changing the HIP treatment temperature to 1700° C. The average crystal grain size of the zirconia sintered body of the present example was 61.3 μm. The evaluation results are shown in Table 2.

Example 17

A zirconia sintered body of the present example was obtained by the same method as in Example 1 except for using an La₂O₃ powder (purity: 99.99%, manufactured by Wako Pure Chemical Industries, Ltd.) in place of the LZO powder, adding the La₂O₃ powder to the zirconia powder in a manner that the weight ratio of the La₂O₃ powder was 10 wt. %, and changing the temperature lowering rate after the HIP treatment to 80° C./min. The average crystal grain size of the zirconia sintered body of the present example was 80.2 μm. The evaluation results are shown in Table 2.

Example 18

A zirconia sintered body of the present example was obtained by the same method as in Example 1 except for using an La₂O₃ powder (purity: 99.99%, manufactured by Wako Pure Chemical Industries, Ltd.) in place of the LZO powder, adding the La₂O₃ powder to the zirconia powder in a manner that the weight ratio of the La₂O₃ powder was 10 wt. %, and changing the temperature lowering rate after the HIP treatment to 20° C./min. The average crystal grain size of the zirconia sintered body of the present example was 40.2 μm, and the three-point bending strength was 827 MPa. The evaluation results are shown in Table 2.

Example 19

A zirconia sintered body of the present example was obtained by the same method as in Example 1 except for using an La₂O₃ powder (purity: 99.99%, manufactured by Wako Pure Chemical Industries, Ltd.) in place of the LZO powder, adding the La₂O₃ powder to the zirconia powder in a manner that the weight ratio of the La₂O₃ powder was 10 wt. %, and changing the temperature lowering rate after the HIP treatment to 10° C./min. The average crystal grain size of the zirconia sintered body of the present example was 88.5 μm. The evaluation results are shown in Table 2.

TABLE 2

| | Composition (mol %) | | | Sintered body density | Average crystallite size | Biaxial bending strength | Fracture toughness $K_{IC}$ (IF) | Transmittance (%) | | |
|---|---|---|---|---|---|---|---|---|---|---|
| | $ZrO_2$ | $Y_2O_3$ | $La_2O_3$ | (g/cm³) | (nm) | (MPa) | (MPa·m$^{0.5}$) | TT | DF | PT |
| Example 1  | 92.69 | 2.57 | 4.73 | 6.074 | 18.8 | 1042 | 1.96 | 61.77 | 24.28 | 37.49 |
| Example 2  | 92.69 | 2.57 | 4.73 | 6.079 | 22.5 | 592  | 2.11 | 61.00 | 55.59 | 4.41  |
| Example 3  | 92.69 | 2.57 | 4.73 | 6.087 | 21.5 | 504  | 2.18 | 62.29 | 32.74 | 29.55 |
| Example 4  | 92.89 | 2.57 | 4.73 | 6.113 | 17.5 | 554  | 2.23 | 60.92 | 33.33 | 27.59 |
| Example 5  | 92.69 | 2.57 | 4.73 | 6.087 | 23.2 | 1295 | 2.10 | 63.26 | 59.77 | 3.49  |
| Example 6  | 92.69 | 2.57 | 4.73 | 6.095 | 23.3 | 905  | 2.03 | 50.74 | 48.06 | 2.68  |
| Example 7  | 93.83 | 2.69 | 3.49 | 6.108 | 21.8 | 832  | 2.24 | 64.64 | 15.20 | 49.44 |
| Example 8  | 93.26 | 2.63 | 4.11 | 6.074 | 21.1 | 1051 | 2.12 | 64.64 | 44.06 | 20.58 |
| Example 9  | 93.26 | 2.63 | 4.11 | 6.082 | 21.8 | 1053 | 2.28 | 60.53 | 29.20 | 31.33 |
| Example 10 | 91.52 | 2.46 | 6.03 | 6.050 | 20.6 | 592  | 1.72 | 65.47 | 37.35 | 28.12 |
| Example 11 | 93.26 | 2.63 | 4.11 | 6.078 | 20.4 | 1301 | 2.12 | 62.75 | 35.14 | 27.61 |
| Example 12 | 91.52 | 2.46 | 6.03 | 6.099 | 16.8 | 916  | 1.82 | 62.96 | 35.96 | 27.00 |
| Example 13 | 92.99 | 2.88 | 4.13 | 6.078 | 20.0 | 1051 | 2.12 | 56.94 | 45.72 | 11.22 |
| Example 14 | 92.99 | 2.88 | 4.13 | 6.090 | 28.2 | 675  | 2.10 | 68.37 | 51.03 | 17.34 |
| Example 15 | 94.04 | 2.91 | 3.05 | 6.086 | 25.7 | 967  | 2.36 | 65.61 | 13.03 | 52.58 |
| Example 16 | 94.04 | 2.91 | 3.05 | 6.103 | 29.8 | 954  | 2.23 | 67.45 | 14.92 | 52.53 |
| Example 17 | 92.99 | 2.88 | 4.13 | 6.052 | 29.7 | 949  | 1.83 | 62.07 | 26.12 | 35.95 |
| Example 18 | 92.99 | 2.88 | 4.13 | 6.081 | 18.9 | 899  | 2.31 | 57.50 | 32.60 | 24.90 |
| Example 19 | 92.99 | 2.88 | 4.13 | 6.089 | 19.0 | 601  | 2.42 | 51.56 | 26.49 | 25.07 |

Example 20

The $La_2O_3$ powder was added to a 4 mol % yttria-containing zirconia powder having a BET specific surface area of 7 m$^2$/g (trade name: TZ-4YS, manufactured by Tosoh Corporation) in a manner that the weight ratio of the $La_2O_3$ powder to the zirconia powder was 5 wt. %, and mixed to obtain a mixed powder. The mixing was performed by wet mixing in an ethanol solvent for 120 hours using a ball mill with zirconia balls having a diameter of 10 mm. The obtained mixed powder was dried in the air at 80° C. to form a source powder.

The source powder was molded by uniaxial pressing by mold pressing to obtain a premolded body. The pressure of the uniaxial pressing was 50 MPa. The obtained premolded body was subjected to cold isostatic pressing (hereinafter, referred to as "CIP") treatment to obtain a cylindrical green body having a diameter of 20 mm and a thickness of approximately 3 mm. The pressure of the CIP treatment was 200 MPa.

The green body was subjected to primary sintering in the atmosphere, at a temperature elevation rate of 100° C./h, a sintering temperature of 1450° C., and for a sintering time of 2 hours to obtain a primary sintered body.

The obtained primary sintered body was placed in a container that was made of zirconia and that had a lid, and subjected to HIP treatment to obtain an HIP-treated body. The HIP-treated body was used as the zirconia sintered body of the present example. The HIP treatment conditions were as follows: in a 99.9% argon gas atmosphere as a pressure medium, temperature elevation rate of 600° C./h, HIP temperature of 1650° C., HIP pressure of 150 MPa, and maintaining time for 1 hour.

After the HIP treatment, an HIP-treated body was obtained by lowering the temperature from the sintering temperature to room temperature. Note that the temperature lowering rate from the HIP temperature to 1000° C. was 83° C./min.

The obtained HIP-treated body was subjected to heat treatment in the air at 1000° C. for 1 hour to obtain a colorless translucent sintered body. The evaluation results of the zirconia sintered body of the present example are shown in Table 3.

Example 21

A zirconia sintered body of the present example was obtained by the same method as in Example 20 except for using a 5 mol % yttria-containing zirconia powder having a BET specific surface area of 7 m$^2$/g (trade name: TZ-5YS, manufactured by Tosoh Corporation) as a zirconia powder of the source material, changing the weight ratio of the $La_2O_3$ powder to 10 wt. %, and changing the HIP treatment temperature to 1750° C. The evaluation results of the zirconia sintered body of the present example are shown in Table 3.

Example 22

A 3 mol % yttria-containing zirconia powder having a BET specific surface area of 7 m$^2$/g (trade name: TZ-3YS, manufactured by Tosoh Corporation) and a 4 mol % yttria-containing zirconia powder having a BET specific surface area of 7 m$^2$/g (trade name: TZ-4YS, manufactured by Tosoh Corporation) as the zirconia powder of the source material were weighed out in a manner that the amount of yttria relative to the amount of zirconia was 3.3 mol %, a $La_2O_3$ powder was added to the zirconia powder in a manner that the weight ratio of the $La_2O_3$ powder was 10 wt. %, and these were mixed to obtain a mixed powder. A zirconia sintered body of the present example was obtained by the same method as in Example 20 except for using the mixed powder and changing the HIP treatment temperature to 1750° C. The evaluation results of the zirconia sintered body of the present example are shown in Table 3.

Example 23

The $La_2O_3$ powder was added to a 3 mol % yttria-containing zirconia powder having a BET specific surface area of 7 m$^2$/g (trade name: TZ-3YS, manufactured by Tosoh Corporation) as the zirconia powder of the source material in a manner that the weight ratio of the $La_2O_3$ powder to the zirconia powder was 7.5 wt. %.

A zirconia sintered body of the present example was obtained by the same method as in Example 20 except for using this mixed powder and changing the HIP treatment temperature to 1750° C. The evaluation results of the zirconia sintered body of the present example are shown in Table 3.

TABLE 3

| | Composition (mol %) | | | Sintered body density | Average crystallite size | Biaxial bending strength | Fracture toughness $K_{IC}$ (IF) | Transmittance (%) | | |
|---|---|---|---|---|---|---|---|---|---|---|
| | $ZrO_2$ | $Y_2O_3$ | $La_2O_3$ | (g/cm$^3$) | (nm) | (MPa) | (MPa·m$^{0.5}$) | TT | DF | PT |
| Example 20 | 94.07 | 3.92 | 2.02 | 6.067 | 254.1 | 623 | 2.20 | 57.49 | 56.89 | 1.10 |
| Example 21 | 91.02 | 4.79 | 4.19 | 6.039 | 241.3 | 560 | 1.34 | 70.01 | 18.47 | 51.54 |
| Example 22 | 92.70 | 3.16 | 4.14 | 6.092 | 120.4 | 642 | 2.47 | 70.78 | 58.26 | 12.52 |
| Example 23 | 94.04 | 2.91 | 3.05 | 6.106 | 105.7 | 617 | 2.42 | 65.16 | 50.89 | 14.27 |

Example 24

A 2.45 mol % yttria-containing zirconia powder was obtained by mixing a 3 mol % yttria-containing zirconia powder having a BET specific surface area of 7 m$^2$/g (trade name: TZ-3YS, manufactured by Tosoh Corporation) and a 2 mol % yttria-containing zirconia powder having a BET specific surface area of 16 m$^2$/g (trade name: TZ-2Y, manufactured by Tosoh Corporation) as the zirconia powder of the source material. A sintered body of the present example was produced by the same method as in Example 1 except for adding the $La_2O_3$ powder to the powder in a manner that the weight ratio of the $La_2O_3$ powder to the powder was 10.5 wt. %. The average crystal grain size of the zirconia sintered body of the present example was 36.9 µm. The evaluation results are shown in Table 4.

Example 25

A 2.5 mol % yttria-containing zirconia powder was obtained by mixing the zirconia powder in the same manner as in Example 24. A sintered body of the present example was produced by the same method as in Example 1 except for using the obtained zirconia powder and changing the weight ratio of the $La_2O_3$ powder to 10 wt. %. The average crystal grain size of the zirconia sintered body of the present example was 54.4 μm. The evaluation results are shown in Table 4.

Example 26

A 2.6 mol % yttria-containing zirconia powder was obtained by mixing the zirconia powder in the same manner as in Example 24. A sintered body of the present example was produced by the same method as in Example 1 except for using the obtained zirconia powder and changing the weight ratio of the $La_2O_3$ powder to 11 wt. %. The average crystal grain size of the zirconia sintered body of the present example was 42.6 μm. The evaluation results are shown in Table 4.

Example 27

A 2.8 mol % yttria-containing zirconia powder was obtained by mixing the zirconia powder in the same manner as in Example 24. A sintered body of the present example was produced by the same method as in Example 1 except for using the obtained zirconia powder and changing the weight ratio of the $La_2O_3$ powder to 10 wt. %. The average crystal grain size of the zirconia sintered body of the present example was 46.3 μm. The evaluation results are shown in Table 4.

Example 28

A 2.8 mol % yttria-containing zirconia powder was obtained by mixing the zirconia powder in the same manner as in Example 24. A sintered body of the present example was produced by the same method as in Example 1 except for using the obtained zirconia powder and changing the weight ratio of the $La_2O_3$ powder to 9.2 wt. %. The average crystal grain size of the zirconia sintered body of the present example was 45.2 μm. The evaluation results are shown in Table 4.

zirconia powder was 10 wt. %. Relative to the total weight of the zirconia powder and the $La_2O_3$ powder, 500 ppm by weight of a CaO powder (manufactured by Wako Pure Chemical Industries, Ltd., 99.9%) was added to obtain a mixed powder. A zirconia sintered body of the present example was obtained by the same method as in Example 20 except for using the mixed powder and changing the HIP treatment temperature to 1750° C. As a result of the XRD measurement, the peak of the crystal phase of the sintered body was only the zirconia peak, and it was confirmed that other crystal phases except the zirconia, such as CaO, were not contained. As a result, it was confirmed that the CaO functioned as a stabilizer similar to the $Y_2O_3$. The obtained sintered body was a colorless translucent sintered body. The composition of the zirconia sintered body of the present example included 92.88 mol % of $ZrO_2$, 2.88 mol % of $Y_2O_3$, 0.12 mol % of CaO, and 4.13 mol % of $La_2O_3$. The average crystal grain size of the zirconia sintered body of the present example was 21.3 μm. The evaluation results of the zirconia sintered body of the present example are shown in Table 5.

Example 30

A zirconia sintered body of the present example was obtained by the same method as in Example 29 except for using a MgO powder (trade name: 500A, manufactured by Ube Material Industries, Ltd.) in place of the CaO powder.

As a result of the XRD measurement, the peak of the crystal phase of the sintered body was only the zirconia peak, and it was confirmed that other crystal phases except the zirconia, such as MgO, were not contained. As a result, it was confirmed that the MgO functioned as a stabilizer similar to the $Y_2O_3$. The obtained sintered body was a colorless translucent sintered body. The composition of the zirconia sintered body of the present example included 92.83 mol % of $ZrO_2$, 2.88 mol % of $Y_2O_3$, 0.17 mol % of MgO, and 4.13 mol % of $La_2O_3$. The average crystal grain size of the zirconia sintered body of the present example was 24.7 μm. The evaluation results are shown in Table 5.

Example 31

The $La_2O_3$ powder was added to a 3 mol % yttria-containing zirconia powder having a BET specific surface area of 7 $m^2/g$ (trade name: TZ-3YS, manufactured by Tosoh

TABLE 4

| | Composition (mol %) | | | Sintered body density | Average crystallite size | Biaxial bending strength | Fracture toughness $K_{IC}$ (IF) | Transmittance (%) | | |
|---|---|---|---|---|---|---|---|---|---|---|
| | $ZrO_2$ | $Y_2O_3$ | $La_2O_3$ | $(g/cm^3)$ | (nm) | (MPa) | $(MPa \cdot m^{0.5})$ | TT | DF | PT |
| Example 24 | 93.32 | 2.34 | 4.34 | 6.090 | 19.96 | 1065 | 2.57 | 54.58 | 47.93 | 6.65 |
| Example 25 | 93.49 | 2.40 | 4.11 | 6.099 | 30.95 | 962 | 2.56 | 62.82 | 23.59 | 39.23 |
| Example 26 | 92.96 | 2.48 | 4.56 | 6.086 | 13.74 | 1207 | 2.43 | 57.98 | 48.34 | 9.64 |
| Example 27 | 93.19 | 2.68 | 4.13 | 6.094 | 21.24 | 1098 | 2.29 | 65.54 | 37.11 | 27.43 |
| Example 28 | 93.53 | 2.69 | 3.78 | 6.092 | 24.28 | 1102 | 2.32 | 64.56 | 37.21 | 27.35 |

Example 29

The $La_2O_3$ powder was added to a 3 mol % yttria-containing zirconia powder having a BET specific surface area of 7 $m^2/g$ (trade name: TZ-3YS, manufactured by Tosoh Corporation) as the zirconia powder of the source material in a manner that the weight ratio of the $La_2O_3$ powder to the zirconia powder was 10 wt. %. Relative to the total weight of the zirconia powder and the $La_2O_3$ powder, 1000 ppm by weight of a γ-alumina powder having a BET specific surface area of 200 $m^2/g$ (trade name: TM-300D, manufactured by Taimei Chemicals Co., Ltd.) was added to obtain a mixed powder. A zirconia sintered body of the present example was obtained by the same method as in Example 1 except for using this mixed powder. The obtained sintered body was a colorless translucent sintered body.

The average crystal grain size of the zirconia sintered body of the present example was 52.1 μm. The three-point bending strength was 856 MPa. The evaluation results are shown in Table 5.

Example 32

A zirconia sintered body of the present example was obtained by the same method as in Example 31 except for adding 250 ppm by weight of an α-alumina powder having a BET specific surface area of 6.7 m²/g (trade name: AKP-30, manufactured by Sumitomo Chemical Co., Ltd.) as the alumina powder. The obtained sintered body was a colorless translucent sintered body. The average crystal grain size of the zirconia sintered body of the present example was 78.5 μm. The three-point bending strength was 842 MPa. The evaluation results are shown in Table 5.

Example 33

A zirconia sintered body of the present example was obtained by the same method as in Example 31 except for adding 500 ppm by weight of an α-alumina powder having a BET specific surface area of 6.7 m²/g (trade name: AKP-30, manufactured by Sumitomo Chemical Co., Ltd.) as the alumina powder. The obtained sintered body was a colorless translucent sintered body. The average crystal grain size of the zirconia sintered body of the present example was 78.5 μm. The three-point bending strength was 844 MPa. The evaluation results are shown in Table 5.

Example 34

The $La_2O_3$ powder was added to a 3 mol % yttria-containing zirconia powder having a BET specific surface area of 7 m²/g (trade name: TZ-3YS, manufactured by Tosoh Corporation) as the zirconia powder of the source material in a manner that the weight ratio of the $La_2O_3$ powder to the zirconia powder was 10 wt. %. The source material powder was molded by uniaxial pressing by mold pressing to obtain a premolded body. The pressure of the uniaxial pressing was 50 MPa. The obtained premolded body was subjected to CIP treatment to obtain a cylindrical molded body having a diameter of 20 mm and a thickness of approximately 3 mm. The pressure of the CIP treatment was 200 MPa.

The green body was subjected to pressureless sintering in the air, at a temperature elevation rate of 100° C./h, a sintering temperature of 1775° C., and for a sintering time of 1 hour to obtain a zirconia sintered body of the present example. The average temperature lowering rate from the sintering temperature to 1000° C. was 16.7° C./min. The average crystal grain size of the zirconia sintered body of the present example was 12.1 μm. The evaluation results are shown in Table 6.

TABLE 6

|  | Composition (mol %) | | | Sintered body density | Average crystallite size | Biaxial bending strength | Fracture toughness $K_{IC}$ (IF) | Transmittance (%) | | |
| --- | --- | --- | --- | --- | --- | --- | --- | --- | --- | --- |
|  | $ZrO_2$ | $Y_2O_3$ | $La_2O_3$ | (g/cm³) | (nm) | (MPa) | (MPa·m^0.5) | TT | DF | PT |
| Example 34 | 92.99 | 2.88 | 4.13 | 6.098 | 18.80 | 1054 | 2.88 | 51.30 | 50.75 | 0.55 |

From Table 6, the sintered body of Example 34 had a biaxial bending strength of 1000 MPa or greater and a total light transmittance of 50% or greater. As a result, it was confirmed that a sintered body having both translucency and strength can be obtained by a one-step sintering method.

Example 35

A zirconia sintered body of the present example was obtained by the same method as in Example 1 except for

TABLE 5

|  | Composition (mol %) | | | $Al_2O_3$ (ppm by weight) | Sintered body density (g/cm³) | Average crystallite size (nm) | Biaxial bending strength (MPa) | Fracture toughness $K_{IC}$ (IF) (MPa·m^0.5) | Transmittance (%) | | |
| --- | --- | --- | --- | --- | --- | --- | --- | --- | --- | --- | --- |
|  | $ZrO_2$ | $Y_2O_3$ | $La_2O_3$ |  |  |  |  |  | TT | DF | PT |
| Example 29 | 92.99 | 3.00*¹ | 4.13 | 0 | 6.002 | 123.4 | 1473 | 2.07 | 69.55 | 62.14 | 7.41 |
| Example 30 | 92.83 | 3.04*² | 4.13 | 0 | 6.006 | 65.72 | 1260 | 2.15 | 68.86 | 55.91 | 12.95 |
| Example 31 | 92.99 | 2.88 | 4.13 | 1000 | 6.082 | 31.86 | 1391 | 2.20 | 63.13 | 36.26 | 26.87 |
| Example 32 | 92.99 | 2.88 | 4.13 | 250 | 6.089 | 23.98 | 1038 | 2.04 | 63.84 | 24.90 | 28.94 |
| Example 33 | 92.99 | 2.88 | 4.13 | 500 | 6.088 | 23.59 | 1087 | 2.50 | 66.23 | 23.55 | 42.68 |

*¹The $Y_2O_3$ concentration of Example 29 was the total of 2.88 mol % of $Y_2O_3$ and 0.12 mol % of CaO
*²The $Y_2O_3$ concentration of Example 30 was the total of 2.88 mol % of $Y_2O_3$ and 0.17 mol % of MgO From Table 5, it was confirmed that a sintered body having both translucency and strength was obtained wherein total light transmittance was 68% or greater and biaxial bending strength was 1200 MPa even when CaO or MgO was used as the stabilizer. Furthermore, it was confirmed that a sintered body having both translucency and strength can be obtained even when alumina was contained.

using an $La_2O_3$ powder (purity: 99.99%, manufactured by Wako Pure Chemical Industries, Ltd.) in place of the LZO powder, adding the $La_2O_3$ powder to the zirconia powder in a manner that the weight ratio of the $La_2O_3$ powder was 10 wt. %, and changing the temperature lowering rate after the HIP treatment to 80° C./min. The results are shown in Table 7.

Figure 11:
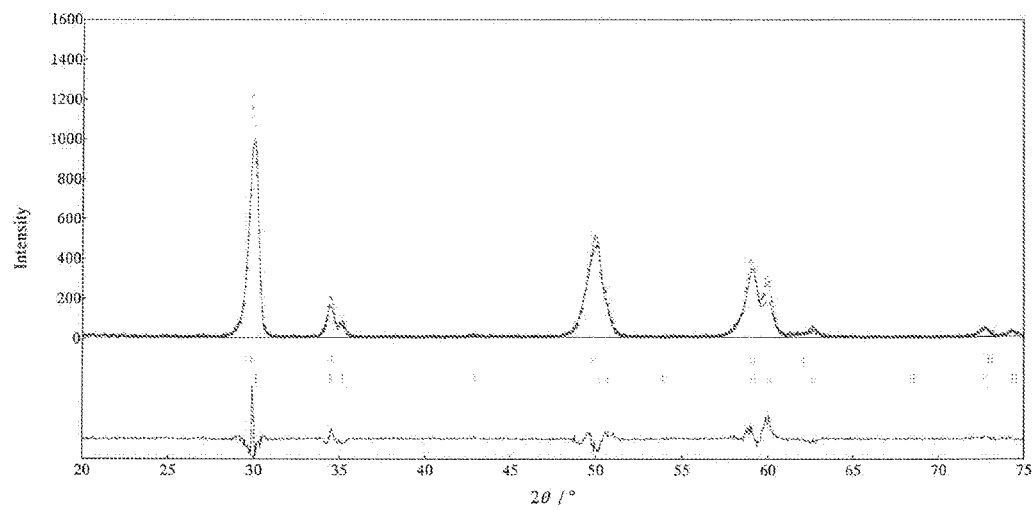
FIG. 11 is the Rietveld analysis result of the XRD pattern of the zirconia sintered body of Example 35.

The Rietveld analysis result of the zirconia sintered body of the present example is shown in FIG. 11, and the TEM observation images are shown in FIGS. 12A to 12D. By the XRD pattern of FIG. 11, it was confirmed that the zirconia sintered body of the present example did not contain lanthanum oxide and the like.

Figure 12:
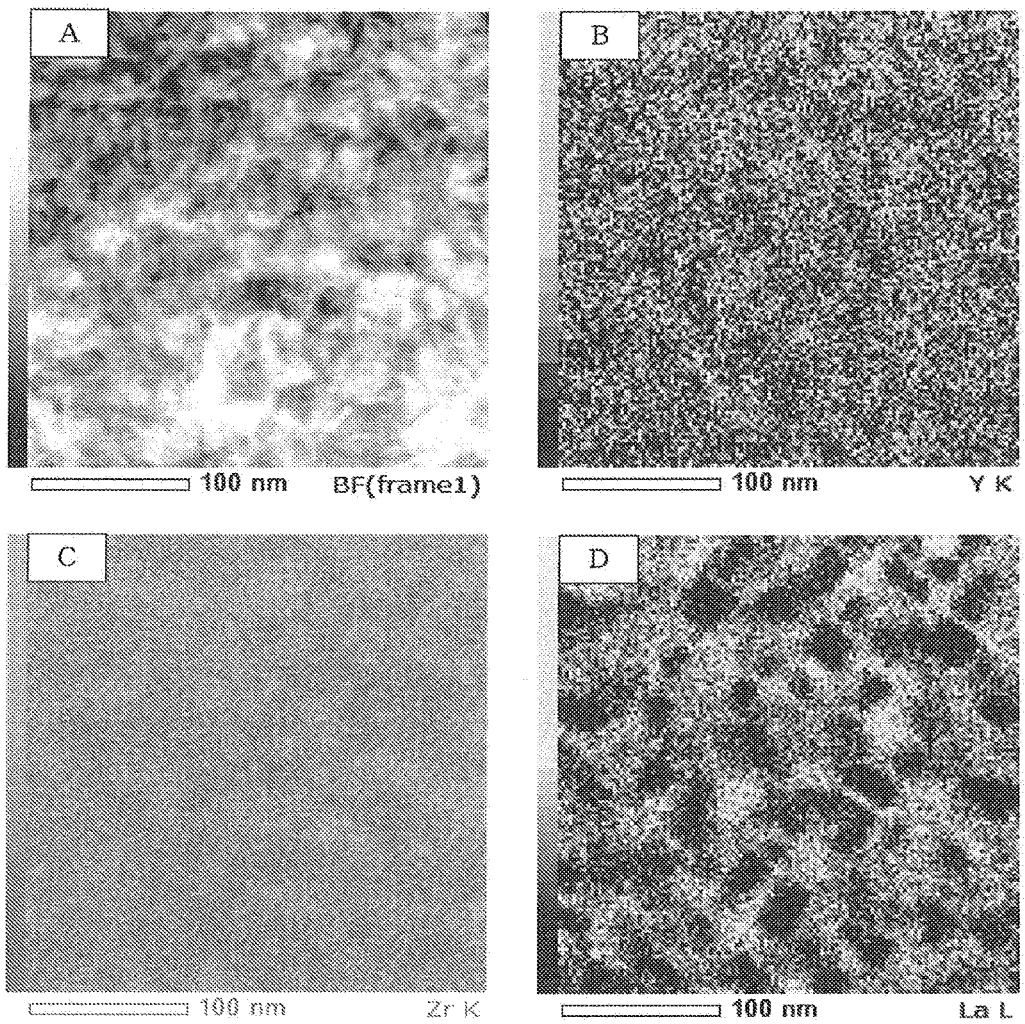
FIGS. 12A to 12D are the TEM observation images of the zirconia sintered body of Example 35 (scale in the figures are 100 nm), where A) is the light view image, B) is the element mapping of yttrium, C) is the element mapping of zirconium, and D) is the element mapping of lanthanum.

Furthermore, from FIG. 12A, the cubic domain and the tetragonal domain of approximately 50 nm were confirmed. The domain was approximately 50 nm while the average crystal grain size was 55.8 μm, and it was confirmed that the domain was smaller than the crystal grain size. By this, it was confirmed that the zirconia sintered body of the present example contained the tetragonal domain and the cubic domain in the crystal grain.

Note that, by the Rietveld analysis, it was confirmed that 68.5 wt. % was the cubic phase and 31.5 wt. % was the tetragonal phase in the zirconia sintered body of the present example, the lattice constant of the cubic phase was a=0.51836 nm, the lattice constant of the tetragonal phase was af=0.51096 nm and cf=0.52067 nm, the crystallite size of the cubic phase was 36 nm, and the crystallite size of the tetragonal phase was 32 nm. Note that, in the Rietveld analysis, the reliability factor was Rwp=18% and S=1.49. The $Y_2O_3$ concentration of the tetragonal phase determined from the lattice constant was 1.27 mol %.

The three-point bending strength was 609 MPa, the fracture toughness $K_{IC}$(SEPB) was 2.74 MPa·m$^{0.5}$, and the thermal conductivity was 1.81 W/mK.

Example 36

A sintered body of the present example was produced by the same method as in Example 35 except for changing the temperature lowering rate from the HIP temperature to 1000° C. to 40° C./min. The three-point bending strength was 893 MPa, and the fracture toughness $K_{IC}$(SEPB) was 2.74 MPa·m$^{0.5}$.

Example 37

A sintered body of the present example was produced by the same method as in Example 35 except for changing the temperature lowering rate from the HIP temperature to 1000° C. to 30° C./min. The three-point bending strength was 1016 MPa, and the fracture toughness $K_{IC}$(SEPB) was 2.93 MPa·m$^{0.5}$.

Example 38

A sintered body of the present example was produced by the same method as in Example 35 except for changing the temperature lowering rate from the HIP temperature to 1000° C. to 20° C./min. The TEM observation images of the present example were shown in FIGS. 13A to 13D. As a result of the XRD measurement, it was found that the zirconia sintered body of the present example did not contain lanthanum oxide and the like.

Figure 13:
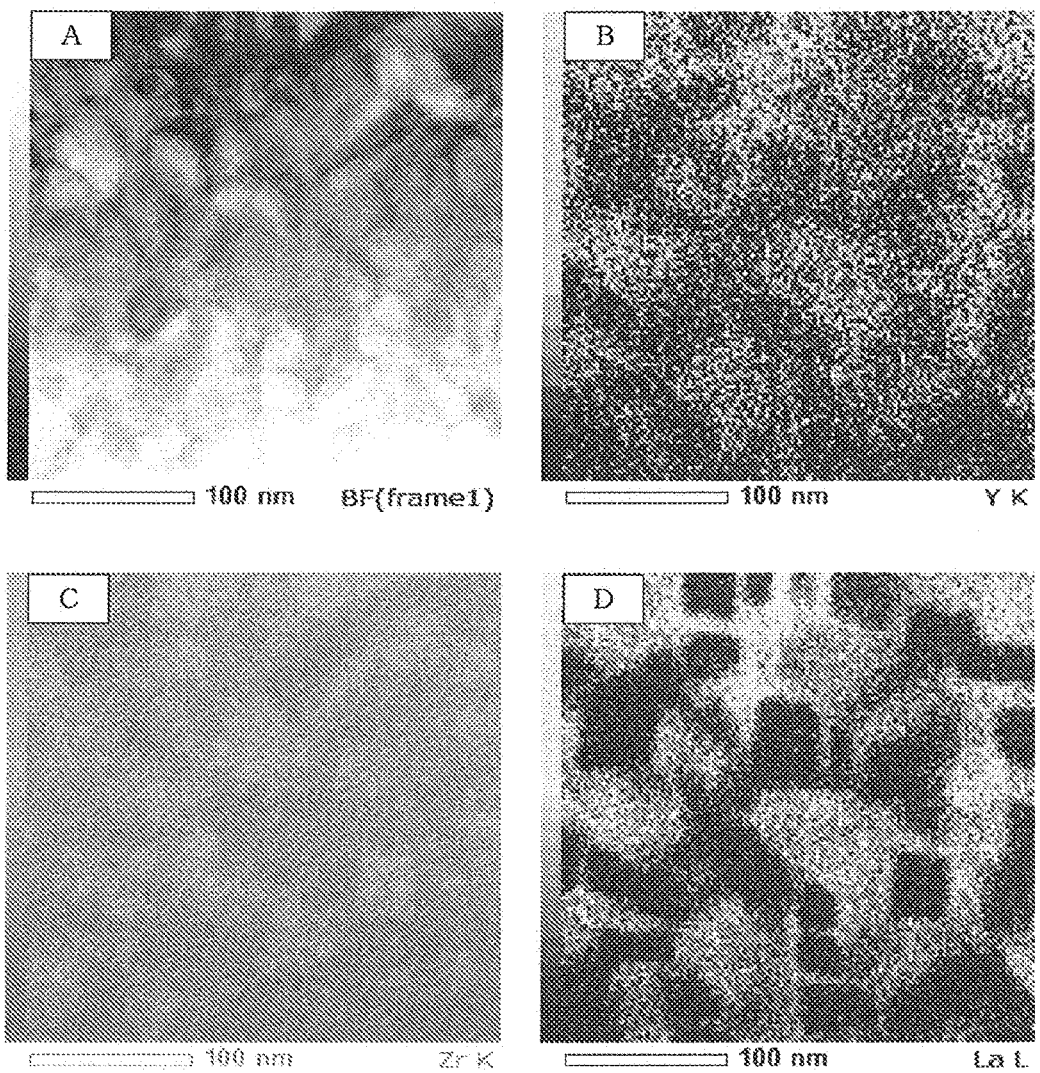
FIGS. 13A to 13D are the TEM observation images of the zirconia sintered body of Example 38 (scale in the figures are 100 nm), where A) is the light view image, B) is the element mapping of yttrium, C) is the element mapping of zirconium, and D) is the element mapping of lanthanum.

Furthermore, from FIG. 13A, the cubic domain and the tetragonal domain of approximately 50 nm were confirmed. The domain was approximately 50 nm while the average crystal grain size was 77.9 μm, it was confirmed that the domain was smaller than the crystal grain size. By this, it was confirmed that the zirconia sintered body of the present example contained the tetragonal domain and the cubic domain in the crystal grain.

Note that, by the Rietveld analysis, it was confirmed that 58.0 wt. % was the cubic phase and 42.0 wt. % was the tetragonal phase in the zirconia sintered body of the present example, the lattice constant of the cubic phase was a=0.51718 nm, the lattice constant of the tetragonal phase was af=0.51082 nm and cf=0.52028 nm, the crystallite size of the cubic phase was 28 nm, and the crystallite size of the tetragonal phase was 35 nm. Note that, in the Rietveld analysis, the reliability factor was Rwp=18% and S=1.40. The $Y_2O_3$ concentration of the tetragonal phase determined from the lattice constant was 1.46 mol %. The three-point bending strength was 895 MPa, and the fracture toughness $K_{IC}$(SEPB) was 3.32 MPa·m$^{0.5}$.

The results of Examples 35 and 38 are shown in Table 7.

TABLE 7

| | Temperature lowering rate (° C./min) | Crystal phase (wt. %) | | Fracture toughness $K_{IC}$ (SEPB) (MPa · m$^{0.5}$) | Three-point bending strength (MPa) |
| --- | --- | --- | --- | --- | --- |
| | | Tetragonal phase | Cubic phase | | |
| Example 35 | 80 | 31.5 | 68.5 | 2.74 | 609 |
| Example 38 | 20 | 42.0 | 58.0 | 3.32 | 895 |

From Table 7, it was confirmed that the tetragonal domain was increased as the temperature lowering rate was slower. Furthermore, along with this, the fracture toughness and the three-point bending strength were made higher. As a result, it was confirmed that the mechanical strength tends to be enhanced by lowering the temperature lowering rate.

Comparative Example 1

The 3 mol % yttria-containing zirconia powder having a BET specific surface area of 7 m$^2$/g (trade name: 3YS, manufactured by Tosoh Corporation) was used as the source material powder of the present comparative example.

The source material powder was molded by uniaxial pressing by mold pressing to obtain a premolded body. By performing the CIP treatment, a cylindrical green body having a diameter of 20 mm and a thickness of approximately 3 mm was obtained. The pressure of the CIP was 200 MPa.

The green body was subjected to primary sintering in the air, at a temperature elevation rate of 100° C./hr, a sintering temperature of 1450° C., and for a sintering time of 2 hours to obtain a primary sintered body.

The obtained primary sintered body was placed in an alumina container having a lid and subjected to HIP treatment. The HIP treatment conditions were as follows: in a 99.9% argon gas atmosphere as a pressure medium, temperature elevation rate of 600° C./hr, HIP temperature of 1750° C., HIP pressure of 150 MPa, and maintaining time for 1 hour.

After the HIP treatment, the HIP treated body was cooled at a temperature lowering rate from the HIP temperature to 1000° C. of 83° C./min.

The obtained HIP-treated body was heat-treated in the air at 1000° C. for 1 hour to obtain a zirconia sintered body of the present comparative example. The average crystal grain size of the obtained zirconia sintered body was 1.80 μm. The evaluation results of the obtained zirconia sintered body are shown in Table 8. The biaxial bending strength of the zirconia sintered body of the present comparative example exhibited high strength exceeding 1 GPa; however, the total light transmittance was 39.00% and the zirconia sintered body had significantly low translucency.

Comparative Example 2

A zirconia sintered body of the present comparative example was obtained by the same method as in Comparative Example 1 except for changing the 8 mol % yttria-containing zirconia powder having a BET specific surface area of 7 m²/g (trade name: 8YS, manufactured by Tosoh Corporation) to the source material powder of the present comparative example.

The average crystal grain size of the obtained zirconia sintered body was 52.9 μm. The evaluation results of the obtained zirconia sintered body are shown in Table 8. The total light transmittance of the zirconia sintered body of the present comparative example was 62.00%, and the zirconia sintered body had high translucency. However, the biaxial bending strength was 253 MPa, and it was confirmed that the sintered body had significantly low strength.

Comparative Example 3

A sintered body was produced by the same conditions as in Comparative Example 1 except for using a 3 mol % yttria-containing zirconia powder having a BET specific surface area of 7 m²/g (trade name: TZ-3YS, manufactured by Tosoh Corporation), adding a LZO powder to the zirconia powder in a manner that the weight ratio of the LZO powder to the yttria-containing zirconia powder was 20 wt. %, and changing the temperature lowering rate in the HIP treatment to 1° C./min.

Figure 9:
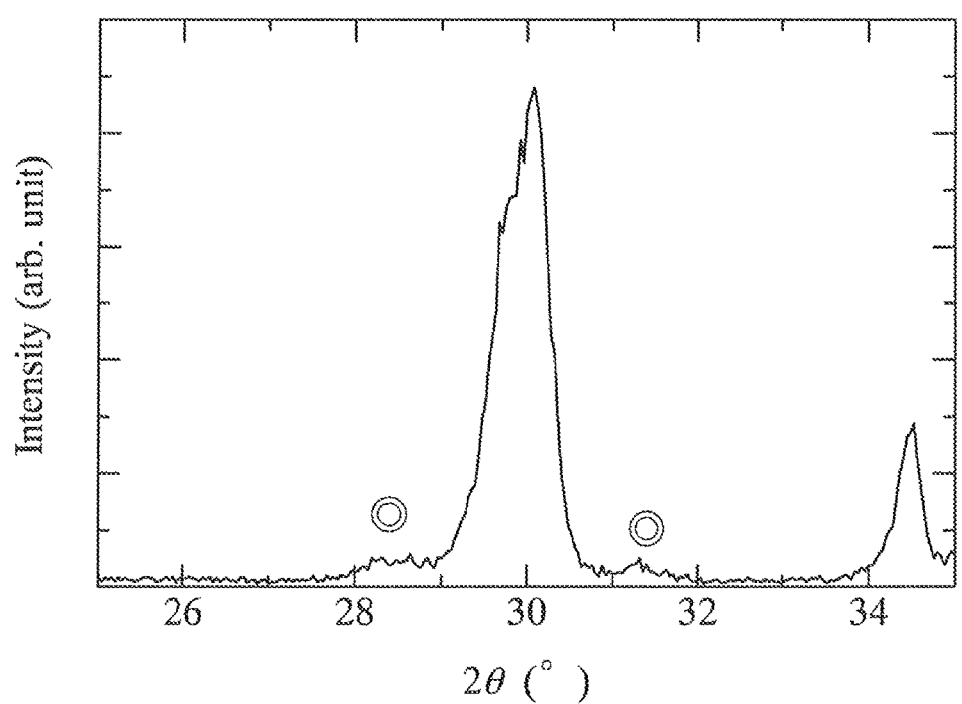
FIG. 9 is the XRD pattern of the zirconia sintered body of Comparative Example 3.

The evaluation results of the zirconia sintered body of the present comparative example are shown in Table 8, and the XRD pattern is shown in FIG. 9. From FIG. 9, it was confirmed that the sintered body of the present comparative example is a zirconia sintered body containing monoclinic phases. Furthermore, the total light transmittance was 44% or less, and the translucency was significantly low.

Comparative Example 4

A zirconia sintered body of the present comparative example was produced by the same conditions as in Comparative Example 1 except for using a zirconia powder having a BET specific surface area of 14 m²/g (trade name: 0Y, manufactured by Tosoh Corporation) and adding a $La_2O_3$ powder (purity: 99.99%, manufactured by Wako Pure Chemical Industries, Ltd.) to the zirconia powder in a manner that the weight ratio of the $La_2O_3$ powder to the yttria-containing zirconia powder was 10 wt. %. Note that the zirconia powder did not contain a stabilizer.

Figure 10:
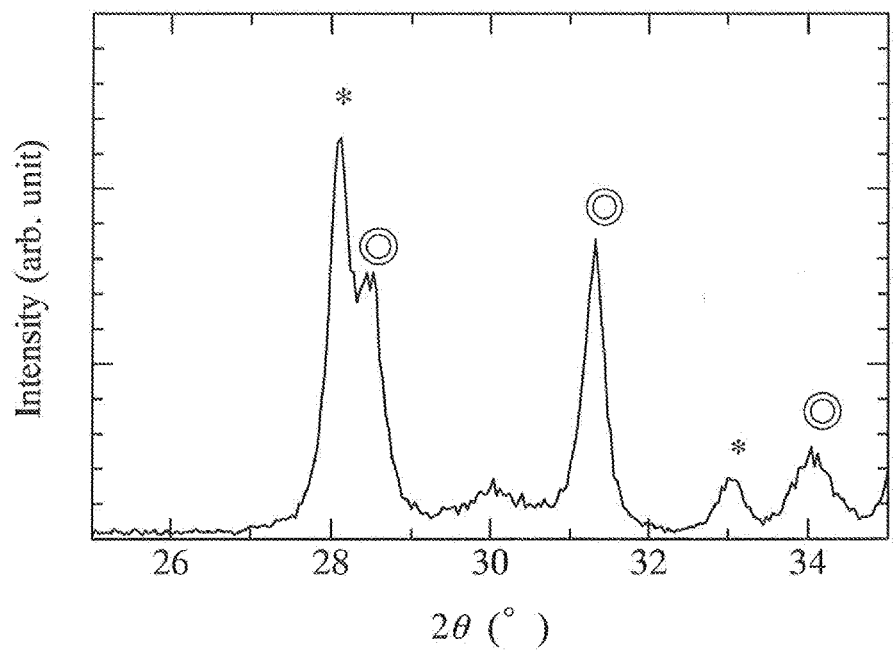
FIG. 10 is the XRD pattern of the zirconia sintered body of Comparative Example 4.

The evaluation results of the zirconia sintered body of the present comparative example are shown in Table 8, and the XRD pattern is shown in FIG. 10. The obtained zirconia sintered body was a sintered body that did not have translucency. Furthermore, from the XRD pattern, it was confirmed that the zirconia sintered body of the present comparative example was a mixed phase of monoclinic phases and $La_2Zr_2O_7$. Furthermore, the zirconia sintered body of the present comparative example did not have a main peak, and the average crystallite size thereof was not determined.

Comparative Example 5

A zirconia sintered body of the present comparative example was obtained by the same method as in Example 1 except for using 10 wt. % of an ytterbium oxide powder in place of 20 wt. % of the LZO powder and using a 3 mol % yttria-containing zirconia powder having a BET specific surface area of 7 m²/g (trade name: TZ-3YS, manufactured by Tosoh Corporation). The results are shown in Table 8. As a result of the XRD measurement, a peak of only zirconia cubic phase was observed in the zirconia sintered body of the present comparative example. As a result, it was confirmed that the zirconia sintered body in which ytterbium, which is a lanthanoid element, was dissolved as a solid solution did not have crystal grains having the cubic domain and the tetragonal domain.

TABLE 8

| | Composition (mol %) | | | Sintered body density (g/cm³) | Average crystallite size (nm) | Biaxial bending strength (MPa) | Fracture toughness $K_{IC}$ (IF) (MPa·m$^{0.5}$) | Transmittance (%) | | |
|---|---|---|---|---|---|---|---|---|---|---|
| | $ZrO_2$ | $Y_2O_3$ | $La_2O_3$ | | | | | TT | DF | PT |
| Comparative Example 1 | 97.00 | 3.00 | 0.00 | 6.076 | 260.0 | 1286 | 4.61 | 39.00 | 38.86 | 0.14 |
| Comparative Example 2 | 92.00 | 8.00 | 0.00 | 5.980 | — | 253 | 1.80 | 62.00 | 24.70 | 37.30 |
| Comparative Example 3 | 92.99 | 2.88 | 4.13 | 5.971 | 14.81 | 692 | 2.38 | 43.59 | 40.40 | 3.19 |
| Comparative Example 4 | 95.97 | 0.00 | 4.03 | 5.634 | —*[1] | — | — | — | — | — |
| Comparative Example 5 | 93.99 | 2.56 | 3.45*[2] | 6.320 | 258.0 | 274 | 1.86 | 37.8 | 37.7 | 0.1 |

*[1]In the table, "—" indicates "unmeasured"
*[2]The $La_2O_3$ content in Comparative Example 5 is the $Yb_2O_3$ content

Example 39

Production of Compound

The $La_2O_3$ powder was mixed to a 3 mol % yttria-containing zirconia powder having a BET specific surface area of 7 m²/g (trade name: 3YS, manufactured by Tosoh Corporation) in a manner that the weight ratio of the $La_2O_3$ powder was 10 wt. %, and then wet-mixed in the same manner as in Example 1 to obtain a mixed powder. The mixed powder, a wax, and an organic binder containing a plasticizer and a thermoplastic resin were mixed to obtain a zirconia compound.

Injection Molding and Production of Sintered Body

The obtained zirconia compound was molded by injection molding to form a plate-like green body having a length of 70 mm, a width of 30 mm, and a thickness of 2 mm. After the organic binder was removed by heating in the air at 450° C., and then sintering was performed in the air at 1450° C. for 2 hours to obtain a primary sintered body. The obtained primary sintered body was placed in a container that was made of zirconia and that had a lid, and subjected to HIP treatment to obtain an HIP-treated body. The HIP-treated body was used as the zirconia sintered body of the present example. The HIP treatment conditions were as follows: in a 99.9% argon gas atmosphere as a pressure medium, temperature elevation rate of 600° C./h, HIP temperature of 1750° C., HIP pressure of 150 MPa, and maintaining time for 1 hour. After the HIP treatment, an HIP-treated body was obtained by lowering the temperature from the sintering temperature to room temperature. Note that the temperature lowering rate from the HIP temperature to 1000° C. was 83° C./min.

The HIP-treated body obtained was subjected to heat treatment in the air at 1000° C. for 1 hour to obtain a colorless translucent sintered body. The obtained sintered body was a zirconia sintered body in which the lanthanum and the yttria were dissolved as a solid solution, and the composition thereof included 92.99 mol % of $ZrO_2$, 2.88 mol % of $Y_2O_3$, and 4.13 mol % of $La_2O_3$. The average crystal grain size was 54.5 μm. The results are shown in Table 9.

Example 40

A sintered body was obtained by the same method as in Example 39 except for changing the primary sintering temperature to 1475° C. The composition of the obtained sintered body included 92.99 mol % of $ZrO_2$, 2.88 mol % of $Y_2O_3$, and 4.13 mol % of $La_2O_3$. The results are shown in Table 9.

Example 41

A sintered body was obtained by the same method as in Example 39 except for changing the primary sintering temperature to 1475° C. and changing the temperature lowering rate from the HIP temperature to 1000° C. to 20° C./min. The composition of the obtained sintered body included 92.99 mol % of $ZrO_2$, 2.88 mol % of $Y_2O_3$, and 4.13 mol % of $La_2O_3$. The average crystal grain size was 35.5 μm. The results are shown in Table 9.

Example 43

An orthodontic bracket formed from a lanthanum-dissolved zirconia sintered body was produced by the same method as in Example 42 except for changing the temperature lowering rate from the HIP temperature to 1000° C. to 30° C./min.

Example 44

An orthodontic bracket formed from a lanthanum-dissolved zirconia sintered body was produced by the same method as in Example 42 except for changing the temperature lowering rate from the HIP temperature to 1000° C. to 20° C./min.

Example 45

An orthodontic bracket formed from a lanthanum-dissolved zirconia sintered body was produced by the same method as in Example 42 except for changing the primary sintering temperature to 1475° C. and the temperature lowering rate from the HIP temperature to 1000° C. to 20° C./min.

Example 46

An orthodontic bracket formed from a lanthanum-dissolved zirconia sintered body was produced by the same method as in Example 42 except for changing the primary sintering temperature to 1475° C., placing the primary sintered body in an unused alumina container during the HIP treatment, and no heat treatment was performed after the HIP treatment. The obtained orthodontic bracket had translucency.

Measurement Example 1 (Torque Strength Test)

The torque strengths of the orthodontic brackets obtained in Examples 42 to 46 were measured. The orthodontic bracket was fixed on a base as a sample, and a stainless steel

TABLE 9

|  | Sintered body density | Average crystallite size | Biaxial bending strength | Fracture toughness $K_{IC}$ (IF) | Transmittance (%) | | |
| --- | --- | --- | --- | --- | --- | --- | --- |
|  | (g/cm³) | (nm) | (MPa) | (MPa · m^{0.5}) | TT | DF | PT |
| Example 39 | 6.100 | 23.8 | 841 | 1.99 | 66.18 | 46.40 | 19.78 |
| Example 40 | 6.086 | 32.2 | 689 | 2.31 | 66.01 | 35.81 | 30.20 |
| Example 41 | 6.091 | 19.2 | 943 | 2.40 | 56.33 | 19.19 | 37.14 |

From these results, it was confirmed that the zirconia sintered body that was equivalent to a zirconia sintered body obtained by press molding was obtained even when injection molding was performed.

Example 42

An orthodontic bracket (length 3.6 mm×width 3.3 mm×height 2.5 mm) formed from lanthanum-dissolved zirconia sintered body was produced by performing the molding, degreasing, sintering, and HIP-treatment in the same manner as in Example 39 except for changing the form of the green body to an orthodontic bracket shape.

wire (0.019×0.025 inches) was passed through a slot portion of the sample to fix the sample. The surface of the slot portion of the sample was in a condition after the HIP treatment. The base was rotated, and the torque strength at the time when the bracket was broken was measured as a torque strength of the sample. Three measurements were performed for each sample, and the average value thereof was used as the torque strength of the sample. The torque strength of the measurement result is shown in Table 10. Furthermore, the torque strength of the orthodontic bracket (length 4.4 mm×width 3.7 mm×height 3.0 mm) formed from translucent alumina used as the orthodontic bracket is also shown in Table 10.

TABLE 10

| | Torque strength (kgf · cm) |
|---|---|
| Example 42 | 0.41 |
| Example 43 | 0.51 |
| Example 44 | 0.52 |
| Example 45 | 0.59 |
| Example 46 | 0.63 |
| Translucent alumina | 0.50 |

It was confirmed that the torque strength of the zirconia sintered body of the present invention was equivalent to the torque strength of a commercially available orthodontic bracket formed from translucent alumina. A larger orthodontic bracket has a higher torque strength. On the other hand, the orthodontic bracket of the examples had the same degree of torque strength although the orthodontic bracket is smaller than a translucent alumina bracket. That is, the zirconia sintered body of the present invention can make the orthodontic bracket even smaller, thereby making the orthodontic bracket not noticeable compared to conventional orthodontic brackets having translucency. Thus, the zirconia sintered body can be used as an orthodontic bracket having excellent aesthetic quality.

Measurement Example 2 (Torque Strength Test)

The orthodontic brackets obtained in Examples 42 and 45 were measured for torque strength in the same manner as in Measurement Example 1 except for using samples in which the surface of the slot portion of the orthodontic bracket was mirror-polished. The results are shown in Table 11.

TABLE 11

| | Torque strength (kgf · cm) | |
|---|---|---|
| | Measurement Example 1 | Measurement Example 2 |
| Example 42 | 0.41 | 0.63 |
| Example 45 | 0.52 | 0.81 |

From the results described above, it was confirmed that the torque strength is enhanced by polishing the slot portion. It was confirmed that the orthodontic bracket of Example 42 had a higher torque strength compared to an orthodontic bracket formed from translucent alumina due to the surface polishing, thereby having practical strength.

Measurement Example 3 (Plasma Etching Test)

Using a reactive plasma etching machine (machine name: DEM-451, manufactured by Anelva), plasma-resistant characteristics of the sample were evaluated. That is, each sample was irradiated with plasma under the following conditions to measure the depth of etching and the etching rate.
Plasma intensity: 300 W
Irradiation duration: 4 hours
Reaction gas: $CF_4$ 25.2 sccm
$O_2$ 6.3 sccm
Ar 126 sccm
As the measurement samples, the zirconia sintered bodies of Examples 1 and 13 were used. Furthermore, quartz glass that has been used as a current semiconductor manufacturing device was used as a comparative sample. Before the measurement, the surface of each sample was subjected to mirror-polishing until the surface roughness became 0.02 μm or less.

After the plasma etching test, the center line average roughness (Ra), maximum height (Ry), and ten-point average height (Rz) of the etched surface of the sample were measured by the method in accordance with JIS B 0601-1994. A laser microscope (instrument name: VK-9500NK-9510, manufactured by Keyence Corporation) was used for the measurement. The results are shown in Table 12.

TABLE 12

| Sample | Depth of etching (μm) | Etching rate (nm/min) | Ra (μm) | Ry (μm) | Rz (μm) |
|---|---|---|---|---|---|
| Example 1 | 2.25 | 9.38 | 0.04 | 0.38 | 0.36 |
| Example 13 | 1.66 | 6.92 | 0.03 | 0.47 | 0.47 |
| Quartz glass | 16.5 | 68.5 | 0.07 | 3.29 | 3.19 |

Ra is the degree of unevenness relative to the average height of the etched surface after the etching, and a greater value indicates more unevenness in the etched surface. Ry indicates the difference between the part on which the etching proceeded the most and the part on which the etching proceeded the least on the etched surface after the etching. A greater value of Ry indicates that a deep etching proceeded locally. Rz indicates the average depth of the unevenness of the etched surface. Thus, a greater value of Rz indicates that the unevenness on the entire etched surface is deeper.

As described above, it was confirmed that the sintered body of the present invention had higher plasma-resistant characteristics compared to those of quartz glass.

INDUSTRIAL APPLICABILITY

The zirconia sintered body of the present invention has both high translucency and high strength. Thus, the zirconia sintered body can be used in dental prosthetic materials or dental components such as components for orthodontics that require aesthetic quality. Furthermore, since the zirconia sintered body of the present invention has excellent design characteristics, the zirconia sintered body can be used as decorative members of timepieces and jewelries as well as plasma-resistant members of components for semiconductor manufacturing devices.

All of the content of the specifications, scopes of patent claims, abstracts, and drawings of Japanese Patent Application No. 2015-005981 filed on Jan. 15, 2015 and Japanese Patent Application No. 2015-233643 filed on Nov. 30, 2015 is cited here and incorporated as a disclosure of the specification of the present invention.

REFERENCE SIGNS LIST

◉: Peak assigned to monoclinic phase zirconia
*: XRD peak assigned to $La_2Zr_2O_7$

The invention claimed is:

1. A zirconia sintered body comprising a crystal grain having a cubic domain and a tetragonal domain, wherein an average crystal grain size is from 12.1 μm to 100 μm, a stabilizer and lanthanum being dissolved as a solid solution in the zirconia sintered body.

2. The zirconia sintered body according to claim 1, wherein an average crystallite size calculated from the full-width at half maximum of $2\theta=30\pm2°$ in a powder X-ray diffraction pattern using CuKα as a radiation source is 255 nm or less.

3. The zirconia sintered body according to claim 1, wherein an average crystallite size calculated from the full-width at half maximum of $2\theta=30\pm2°$ in a powder X-ray diffraction pattern using CuKα as a radiation source is 100 nm or less.

4. The zirconia sintered body according to claim 1, wherein a lanthanum content is 1 mol % or greater but 10 mol % or less.

5. The zirconia sintered body according to claim 1, wherein the stabilizer is a member selected from the group consisting of yttria, scandia, calcia, magnesia, ceria, and mixtures thereof.

6. The zirconia sintered body according to claim 1, wherein bending strength is 500 MPa or greater.

7. The zirconia sintered body according to claim 1, wherein a total light transmittance using illuminant D65 as a radiation source is 45% or greater when a sample thickness is 1 mm.

8. A method of manufacturing the zirconia sintered body described in claim 1, the method comprising:

obtaining a mixed powder by mixing a zirconia source, a stabilizer source, and a lanthanum source;

obtaining a green body by molding the obtained mixed powder;

obtaining a sintered body by sintering the obtained green body at a sintering temperature of 1650° C. or higher; and lowering the temperature from the sintering temperature to 1000° C. at a temperature lowering rate exceeding 1° C./min.

9. The manufacturing method according to claim 8, wherein the sintering comprises a primary sintering of obtaining a primary sintered body by sintering at 1000° C. or higher but lower than 1650° C., and a secondary sintering of sintering the primary sintered body at 1650° C. or higher.

10. A dental component comprising the zirconia sintered body described in claim 1.

* * * * *